(12) United States Patent
Kaldor et al.

(10) Patent No.: US 7,392,142 B2
(45) Date of Patent: Jun. 24, 2008

(54) METHOD TO DETERMINE PREDICTIVE TESTS AND DEVICE APPLYING SAME TO LUBRICANT FORMULATIONS

(75) Inventors: Andrew Kaldor, Warren, NJ (US); Andrew Jackson, Pennington, NJ (US); Manuel Anthony Francisco, Phillipsburg, NJ (US); Phiroz Maneck Bhagat, Westfield, NJ (US); Eugenio Sanchez, Turnersville, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 11/495,370

(22) Filed: Jul. 28, 2006

(65) Prior Publication Data
US 2007/0032964 A1   Feb. 8, 2007

Related U.S. Application Data

(60) Provisional application No. 60/703,732, filed on Jul. 29, 2005.

(51) Int. Cl.
*G01N 33/28* (2006.01)
*G06F 19/00* (2006.01)

(52) U.S. Cl. .............................. 702/22; 702/25; 702/189

(58) Field of Classification Search ................... 702/22, 702/30, 31, 35, 25, 185, 189, 114, 34; 706/2, 706/15, 21
See application file for complete search history.

(56) References Cited

U.S. PATENT DOCUMENTS

| | | | |
|---|---|---|---|
| 5,638,382 A * | 6/1997 | Krick et al. ................. | 714/733 |
| 6,072,576 A * | 6/2000 | McDonald et al. .......... | 356/300 |
| 6,358,894 B1 | 3/2002 | Leta et al. | |
| 6,546,782 B1 * | 4/2003 | De La Cruz et al. ............ | 73/7 |
| 2005/0092072 A1 | 5/2005 | Wollenberg et al. | |
| 2005/0094717 A1 | 5/2005 | Wollenberg et al. | |
| 2005/0095714 A1 | 5/2005 | Wollenberg et al. | |
| 2005/0095716 A1 | 5/2005 | Wollenberg et al. | |
| 2005/0095718 A1 | 5/2005 | Wollenberg et al. | |
| 2005/0096895 A1 | 5/2005 | Wollenberg et al. | |
| 2005/0178190 A1 | 8/2005 | Wollenberg | |
| 2005/0181512 A1 | 8/2005 | Wollenberg | |
| 2005/0181515 A1 | 8/2005 | Wollenberg | |
| 2005/0182572 A1 | 8/2005 | Wollenberg | |
| 2007/0039378 A1 | 2/2007 | Wollenberg | |
| 2007/0068228 A1 | 3/2007 | Wollenberg | |

* cited by examiner

*Primary Examiner*—Bryan Bui
(74) *Attorney, Agent, or Firm*—Robert A. Migliorini

(57) ABSTRACT

The present invention is directed to a method that determines the necessary and sufficient tests to relate a variety of apparently non-related tests to desired final test results. The present invention also provides a method to determine those tests which, having been shown capable to be used in a high-throughput environment, are able to predict end-use qualification test results for lubricants, greases or industrial fluids. As a corollary, the present invention provides a method to select lubricant formulations and components based on apparently non-related, but predictive tests. In an applied example, the present invention is directed to a device and method that produces and evaluates formulated lubricants, functional fluids, and greases by determining previously unknown relationships between Intermediate Tests and End-use Tests.

22 Claims, 13 Drawing Sheets

| | | Intermediate Tests | | | | | | |
|---|---|---|---|---|---|---|---|---|
| | | $t^1$ | $t^2$ | $t^3$ | $t^4$ | ... | $t^n$ | |
| Samples or Components Elemental Set | $s_A$ | $x^1_A$ | $x^2_A$ | $x^3_A$ | $x^4_A$ | ... | $x^n_A$ | $e_A$ |
| | $s_B$ | $x^1_B$ | $x^2_B$ | $x^3_B$ | $x^4_B$ | ... | $x^n_B$ | $e_B$ |
| | $s_C$ | $x^1_C$ | $x^2_C$ | $x^3_C$ | $x^4_C$ | ... | $x^n_C$ | $e_C$ |
| | $s_D$ | $x^1_D$ | $x^2_D$ | $x^3_D$ | $x^4_D$ | ... | $x^n_D$ | $e_D$ |
| | ⋮ | ⋮ | ⋮ | ⋮ | ⋮ | ⋱ | ⋮ | ⋮ |
| | $s_m$ | $x^1_m$ | $x^2_m$ | $x^3_m$ | $x^4_m$ | ... | $x^n_m$ | $e_m$ |

Intermediate Test Results Elemental Set

Schematic of a single hidden layer back-propagation, feed-forward neural network

METHOD TO DETERMINE PREDICTIVE TESTS AND DEVICE APPLYING SAME TO LUBRICANT FORMULATIONS

CROSS REFERENCE TO RELATED APPLICATION

This application claims the benefit of U.S. Provisional Application No. 60/703,732 filed Jul. 29, 2005.

FIELD OF THE INVENTION

The present invention is directed to a method that determines the necessary and sufficient tests to relate a variety of apparently non-related tests to desired final test results. The present invention also provides a method to determine those tests which, having been shown capable to be used in a high-throughput environment, are able to predict end-use qualification test results for lubricants, greases or industrial fluids. As a corollary, the present invention provides a method to select lubricant formulations and components based on apparently non-related but predictive tests. In an applied example, the present invention is directed to a method and a device that produces and evaluates formulated lubricants, functional fluids, and greases by determining previously unknown relationships between Intermediate Tests and End-use Tests.

BACKGROUND OF THE INVENTION

Lubricant, grease and industrial fluid formulation research has long been acknowledged as a combination of art and science. Formulation research presents a nearly overwhelming number of variables for each possible application. Even within a given application area, a wide variety of base fluids may be used. For instance, base fluids are produced to meet required specifications. These base oils are classified by the American Petroleum Institute (API) as Group I, Group II, Group III, Group IV and Group V, which designate parametric boundaries for viscosity index, sulfur content, amount of non-paraffins and the like. However, the actual chemical composition of a base oil that meets a specific API group criteria may vary significantly from base oil to base oil.

Compounding these issues are the vast variety of chemical additives which have become necessary components in today's modern lubricants. For example, lubricants commonly include additives for corrosion control, metal passivation, extreme pressure resistance, viscosity modification, detergency, acid control, etc. While one might correctly assume that the chemistries among these functional groups may vary widely, it is also recognized that the chemistries within each of these functional additive groups may vary significantly. While the properties of any one additive in any one base oil may be relatively well known, combining additives may have unexpected (beneficial or undesired) chemical interactions.

Lubricant research might be somewhat simplified if it was limited to solving this myriad of chemical interactions between additives and base oils. But in the real world, varying engine configurations presents unique flow and heat transfer properties that cause even a standardized lubricant to react differently. Currently, equipment manufacturers require that actual engine or machinery tests verify the applicability of a candidate lubricant formulation. Indeed, many Original Equipment Manufacturers (OEM) of engines or other equipment that employ lubricants, greases or functional fluids, have their own unique test to "qualify" the candidate product. Tests such as the European Union Association des Constructeurs Europeens d'Automobiles (ACEA) standards, or the United States American Petroleum Instititute (API) and International Lubricant Standards Approval Committee (ILSAC) standards require large quantities of the candidate fluids tested over weeks of time under actual full-scale engine conditions. These tests are time consuming and costly.

Lubricant researchers often employ a number of lowest-common-denominator bench tests to attempt to predict how a lubricant would fare in real-world conditions. Such bench tests are designed to provide in a laboratory environment a measure of a property or performance feature of a lubricant sample. The researcher attempts to use the bench test to make a laboratory model of the conditions of actual engines or equipment. Usually, the scope of the bench tests is limited to attempting to re-create one specific aspect of the equipment's operating environment. Not being able to exactly match the intense pressure, heat, friction, load and other conditions of operating equipment, researchers make assumptions to design bench tests to isolate the variable of interest. Unfortunately, it is generally acknowledged that bench tests are, at best, weakly predictive of the single dimension of equipment conditions they attempt to mimic.

Examples of these tests are as follows: ASTM D2266 (Four Ball method for wear preventive characteristics of lubricating grease), ASTM D2272 (Oxidation stability of by rotating bomb), ASTM D2596 (Four Ball method for measurement of load carrying capacity of lubricating grease), ASTM D2783 (Four Ball method for measurement of extreme-pressure properties of lubricating fluids), ASTM D4172 (Four Ball method for wear preventive characteristics of lubricating fluids), ASTM D4742 (Thin-film oxygen uptake test), ASTM D6138 (Emcor test for determination of corrosion preventive properties of lubricating grease under dynamic wet conditions), ASTM D6186 (Pressure differential scanning calorimetry method for oxidation induction time of lubricating oils) along with the numerous other tests specified in various lubricant oil or grease specifications.

These tests too often show poor correlation to real-world results. Since these tests tend to investigate along a single dimension, they limit opportunities to discover positive or negative chemical interactions. Moreover, it is difficult, if not impossible, to determine which combination of tests, if any, would predict a binary pass/fail result for any specific OEM's end-use test. These tests would most likely not give a graduated view of which base oils, additives or formulations would better pass a given OEM end-use test.

The present invention addresses these, and many other issues. Specifically, the present invention provides a method to determine which laboratory scale tests are predictive of real-world results or OEM end-use tests. While the inventors believe that best candidate laboratory-scale tests would be those that produce significant amounts of data, the present invention also details a method of using data in currently existing databases to predict which test, or functional combination of tests, would best predict OEM end-use tests or real world performance results.

One feature of the present invention is that it provides a means to determine which tests, useful in a laboratory setting, would be sufficient to predict the desired end-use qualifying test results. Another feature of the present invention is that it demonstrates a method and a device to predict and select voluminous data-producing tests that will mimic the lubricant bench test results or the end-use qualifying test results. As a corollary, the present invention provides a method to determine which tests, capable of being used in a high-throughput environment, are able to predict end-use qualification test results for lubricants oils and greases. Still yet another feature of the present invention is its ability to employ historical databases of bench test results to select combinations of those bench tests, with and without high-throughput tests, that more accurately predict the end-use qualifying test results.

One embodiment of the present invention employs pattern recognition-based modeling to guide adaptive learning systems to derive correlative models by learning from data. The present invention's use of iterative learning leads to converged functional classifications and/or correlations between independent and dependent variables.

Throughout this application, the inventors use of the word lubricant (or its derivatives) also refers to lubricants, greases, and various types of functional fluids (and their respective derivatives).

The current state of the art for the formulation of lubricants requires extensive formulator experience to select the optimum combination of additives and base stocks. The possible combinatorial space is quite large consisting of many different base oils and "functional families" of additives (e.g., antiwear, antioxidants, antifoaming, viscosity modifiers, dispersants, thickeners, detergents, etc.). Each functional family contains numerous different chemistries to achieve the desired function. Further complicating the formulation discovery process is that the base oils for the lubricant vary widely from highly naphthenic API Group I base oils to high purity PAO to even non-hydrocarbon based fluids such as silicones. Another complication is that the additive functional families may react differently to different base oil combinations. Indeed, one other well-known problem is that lubricant formulation chemistries are not always linear—that is, an interpolated blend of two successful lubricant chemistries does not always produce a product able to pass the same tests.

Creating a new or "step-out" lubricant formulation is severely limited by the extensive in-place engine or machinery testing that each successful candidate lubricant must pass. On average, each individual test costs between $10,000-$150,000. Sole reliance on expensive, large-scale testing to develop new lubricants (and greases), results more often in incremental formulation improvements and limits the inclusion of new, experimental components in new formulations since they require more extensive testing. Overall, sole reliance on expensive large-scale testing confines experimentation more often to the limited known-formulation performance, and it is likely that opportunities for step-out improvements in formulation technology for lubricants, functional fluids or greases are not captured.

The introduction of intermediate bench tests to lubricant formulation research can further complicate the process. Lubricant bench-tests attempt to mimic essential portions of the engine's or industrial equipment's operation, usually limiting themselves to a single dimension (e.g. acid value increase in a stability test at certain temperature. For example, engines may vary significantly within a product category (commercial, personal vehicle, aviation, marine or stationary industrial engines), let alone compared to other types of equipment such as, gearboxes, pumps, compressors, circulating systems and others. Any individual bench test predictive for any one engine is almost certainly not predictive of other engines or machinery.

A further complication is that equipment manufacturer's lubricant qualification tests differ even for similar equipment and are often changed on a frequent basis to reflect updated equipment technology. Typically, lubricant bench-testing is called upon to predict a large range of possible outcomes. While lubricant bench-tests are intended to allow an inexpensive measure of predictability for the more expensive large-scale tests, understanding and interpreting the correlations between bench tests and the final engine or machinery tests has often proven to be difficult. Years of experience, combined with a formulator's intuition, can help to link a successful set of bench tests to a successful large-scale, end-use test or tests. However, even upon entering the 21st century, the formulation of lubricants, functional fluids or greases remains both an art and a science.

Among other features, the present invention provides a unique opportunity to apply high throughput techniques to lubricant research. Researchers have traditionally attempted to use a series of bench tests to determine the potential performance of a formulated lubricant, functional fluid or grease candidate in end-use tests. Commonly used bench tests include wear, viscosity, thermal and oxidative stability, deposit control, elastomer compatibility, filterability, friction, volatility, foam and air release, corrosion and rust, miscibility, solubility and homogeneity and visual appearance. However, these bench tests were seldom adaptable to producing large amounts of data in short periods of time as they often required large lubricant sample volumes, long test times, severe test conditions or combinations of all three. Even if one could easily adapt these bench tests to produce large volumes of data in a short period of time, there is no reason to believe that they would correctly predict actual success on end-use qualifying tests.

SUMMARY OF THE INVENTION

Figure 1:
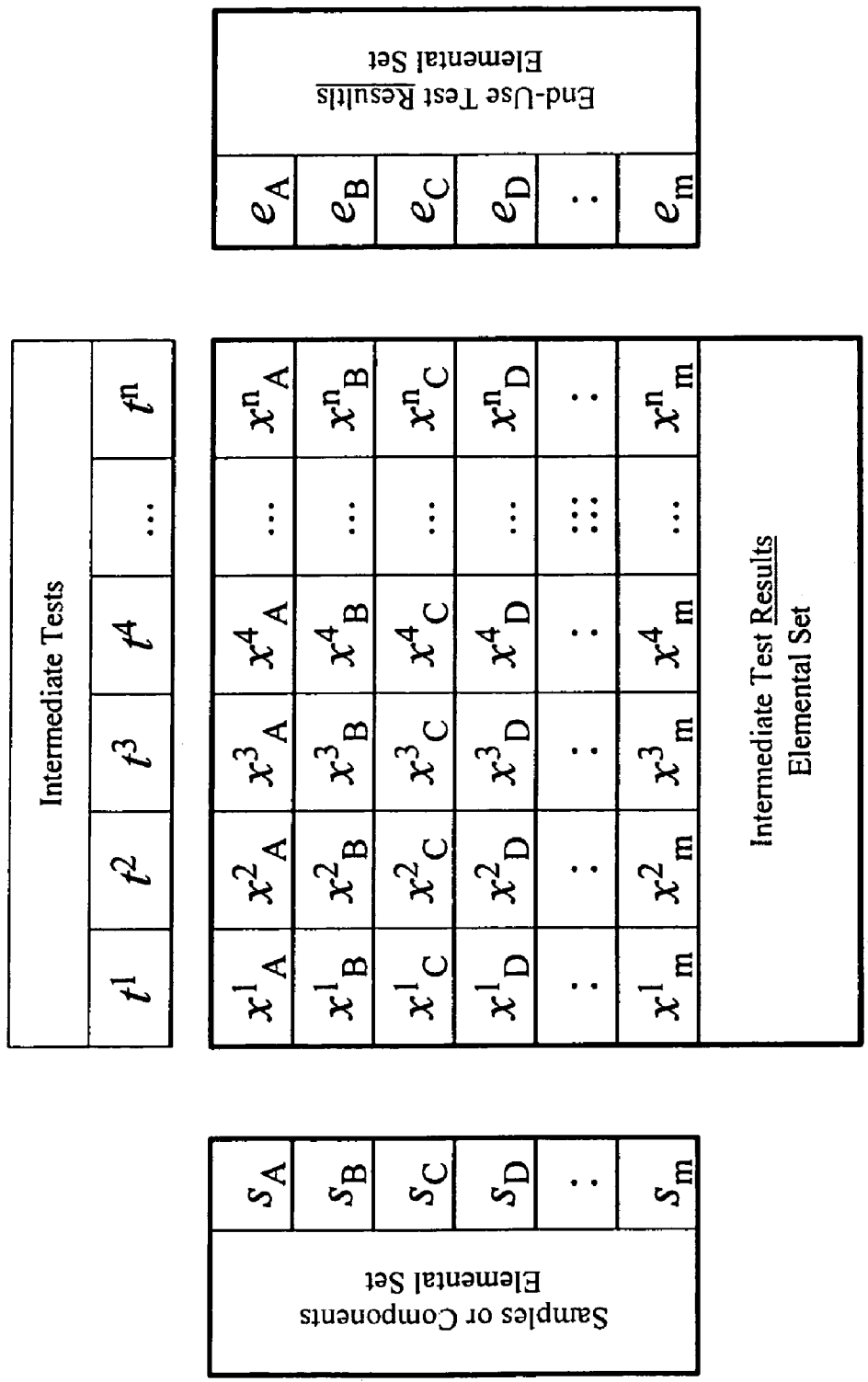
FIG. 1 is a diagram illustrating the Elemental Sets for the current method that relate lubricant "intermediate" testing to final end-use qualifying test results.

A method to determine which members, individually or in combination, of an Elemental Set of Intermediate Tests are predictive of an Elemental Set of End-Use Test Results, the method comprising:
  providing an Elemental Set of Samples having at least a first member and a second member;
  providing an Elemental Set of End-Use Test Results for said Elemental Set of Samples, the Elemental Set of End-Use Tests Results, having at least a first and a second member, such that the first member of said Elemental Set of End-Use Test Results corresponds to said first member of said Elemental Set of Samples and said second member of said Elemental Set of End-Use Tests Results corresponds to said second member of said Elemental Set of Samples, wherein said first member of each set is not the same as the second member of each set;

selecting an Elemental Set of Intermediate Tests having a plurality of members;

obtaining from said selected Elemental Set of Intermediate Tests, a set of Intermediate Test Results; and subjecting the Intermediate Test Results, individually or in combination, to regression analysis to determine which of the members of the Elemental Set of Intermediate Tests is predictive of the Elemental Set of End-Use Test Results for the Elemental Set of Samples.

The present invention is directed to a method that determines the necessary and sufficient tests to relate intermediate tests to final end-use qualifying tests for lubricants.

Another feature of the present invention is that it demonstrates a method to predict and select voluminous data-producing tests that will emulate the lubricant bench test results or the end-use qualifying test results.

As a corollary, the present invention provides a method to determine which tests, capable to be used in a high-throughput environment, are able to predict end-use qualification test results for lubricants.

In a more specific embodiment, the present invention is directed to a method that produces and evaluates formulated products that would pass end-use qualifying tests for lubricants.

In another embodiment, the present invention relates to a method that rapidly, in parallel or serial, tests small samples of formulated products for at least one of following properties or performance features:

1. Wear
2. Friction
3. Viscosity
4. Oxidative Stability
5. Thermal Stability
6. Sludge, varnish and deposit formation
7. Elastomer compatibility
8. Volatility
9. Corrosion and Rust
10. Miscibility or solubility
11. Visual appearance
12. Chemical Composition (Polarity)
13. Scuffing
14. Acidity Increase
15. Soot Formation
16. Storage Stability
17. Hydrolytic Stability
18. Color-Light Stability
19. Low Temperature Fluidity
20. Demulsibility
21. Emulsibility
22. Foam Formation
23. Air Entrainment
24. Acute Toxicity and then determines which of those tests (or functional combinations thereof) are predictive of some other desired result(s).

In another embodiment, the present invention relates a method to determine "step-out" formulations or additives from known useful intermediate tests and end-use results.

DETAILED DESCRIPTION OF THE INVENTION

The present invention provides a techniques developed to rapidly produce and evaluate lubricant candidates to determine their probable success in bench testing, and end-use engine or equipment testing. One feature of the present invention is a method that determines which types of intermediate tests correlate to specific end-use qualifying tests. More specifically, the present invention provides a method to determine those tests which, having been shown capable to be used in a high-throughput environment, are able to predict end-use qualification test results for lubricants. A second feature of the present invention is that it provides a method to combine historical or new bench test data and select combinations of bench tests that are predictive of specific end-use lubricant qualification tests.

A third feature of the present invention is that once appropriate intermediate tests are selected, mathematical models and variable selection algorithms may be employed to correlate those results to selected performance features. This methodology results in extracting features from the experimental results, yielding information that enable formulations that satisfy the end-use qualification tests. Hence the present invention can predict the components for formulations that will lead to successful end-use qualifying test results.

Referring to the Figures, FIG. 1 is a diagram indicating the stages of the current method that relate lubricant "intermediate" testing to final end-use qualifying test results. The diagram lists three Elemental Sets: a "Samples" or "Component" Elemental Set, an "Intermediate Tests" Elemental Set and an "End-Use Test Results" Elemental Set. When the members of any two of these Elemental Sets are defined, the method of the current invention allows one to determine the more predictive members of the third Elemental Set.

For the purposes of the present invention, any item that would fit into any of the boxes of FIG. 1 would be considered a member of that Elemental Set. Therefore, any one test result of an end-use qualifying test would be a member of the Elemental Set of End Use Test Results. Similarly, each sample, or component of a sample, would be a member of the Elemental Set of all Samples or Components. For example, in one embodiment of the present invention, the candidate samples and their formulations would constitute the "Sample" Elemental Set. How each of those samples performed on the end-use qualifying tests would populate the "End-use Results" Elemental Set. The members of the "End-use Results" Elemental Set may include a simple pass/fail determination of the end-use qualifying test or may give more detailed indications of the quality of passing the test. The present invention applies equally well in either situation.

Once these known inputs are selected for the Samples Elemental Set and End-Use Results Elemental Set, a set of intermediate tests is chosen to form the Intermediate Tests Elemental Set. While this choice could be made randomly, one of ordinary skill in the art may also choose a set of Intermediate Tests which they expect might be more predictive than a random selection. These tests may be classical bench tests, but in this embodiment, it is preferred that the tests be capable of being performed in a high throughput environment.

While several useful examples of specific tests created by this method are provided later in this application, any set of tests may be applied. A preferred set of tests would be those tests that would produce high quantities of data over large ranges. For example, FTIR testing, UV tests and mass spectrometry tests may be considered particularly useful in that they readily provide significant amounts of information for each sample. One of ordinary skill in the art would easily be able to discern other tests usable in a high throughput environment that would also produce numerous members of the Intermediate Test Results Elemental Set.

The present invention determines which of the selected set of Intermediate Tests more successfully relates one of the defined Elemental sets to the other defined Elemental Set. While the present method works as long as each Elemental Set has at least two members, the more members of each Elemental Set, the better the predictive results of the method.

Once an Elemental Set of Intermediate Tests has been selected, those intermediate tests are run on each sample. These results are then analyzed using any variety of modeling techniques. Some simple non-limiting examples of modeling techniques include generalized linear regressions such as multiple linear regression, principal components, ridge regression, each of which is encompassed by this invention. For more complex data sets non-linear regression techniques such as neural networks may be employed. One of ordinary skill in the art is well aware of other modeling techniques that could easily be employed with the present invention.

The inventors note that most regression models intended to assess a pass/fail criteria are fully encompassed in this discovery. For example, neural networks, principal component regression, and other linear or non-linear regression models could be written in the general form:

$e_A = F(x^1_A, x^2_A, x^3_A, \ldots, x^n_A) + \epsilon$ or $e_A = F(X_A) + \epsilon$; where $X_A = (x^1_A, x^2_A, x^3_A, \ldots, x^n_A)$ Predicted Performance=$F(X_A)=F(x^1_A, x^2_A, x^3_A, \ldots, x^n_A)$ $\epsilon$: Error term, comprising of errors in the $e_A$, $x^i_A$ and F lack-of-fit If Passing Criterion is, e.g.,: $e_A < F_0$ Predicting Passing Criteria based on $x^i_A$: $F(x^1_A, x^2_A, x^3_A, \ldots, x^n_A) < F_0$, where "F" is a continuous performance-predicting function of "n" variables, "A" is one member of the Elemental Set of Samples, $x^1_A$ is the result of the first Intermediate Test performed on Sample "A", "$e_A$" is the member of the End User Test Elemental set corresponding to Sample "A", and $F_0$ is the pass/fail threshold. For such a model, there exists a subspace, or region, in the $(x^1, x^2, X^3, \ldots, x^n)$ "space" (the space of Intermediate Tests results) that maps, through the function F, to the passing criteria. This can be extended to multiple criteria by choosing different values of $F_0$, thereby creating different boundaries in the Intermediate Test Space which delimit different levels of lubricant performance.

As more criteria levels are added, in the limit, all known regression models are a subset of this generalized boundary-based classification approach. As non-limiting examples, Principal Component Regression, Multiple Linear Regressions and Neural Net Regressions fit into this model. One embodiment of the present invention uses a back propagating neural net. Back-propagation (or "backprop") neural nets are comprised of inter-connected simulated neurons. A neuron is an entity capable of receiving and sending signals and is simulated by software algorithms on a computer. Each simulated neuron (i) receives signals from other neurons, (ii) combines these signals, (iii) transforms this signal and (iv) sends the result to yet other neurons. Typically, a weight, modifying the signal being communicated, is associated with each connection between neurons.

Figure 2:
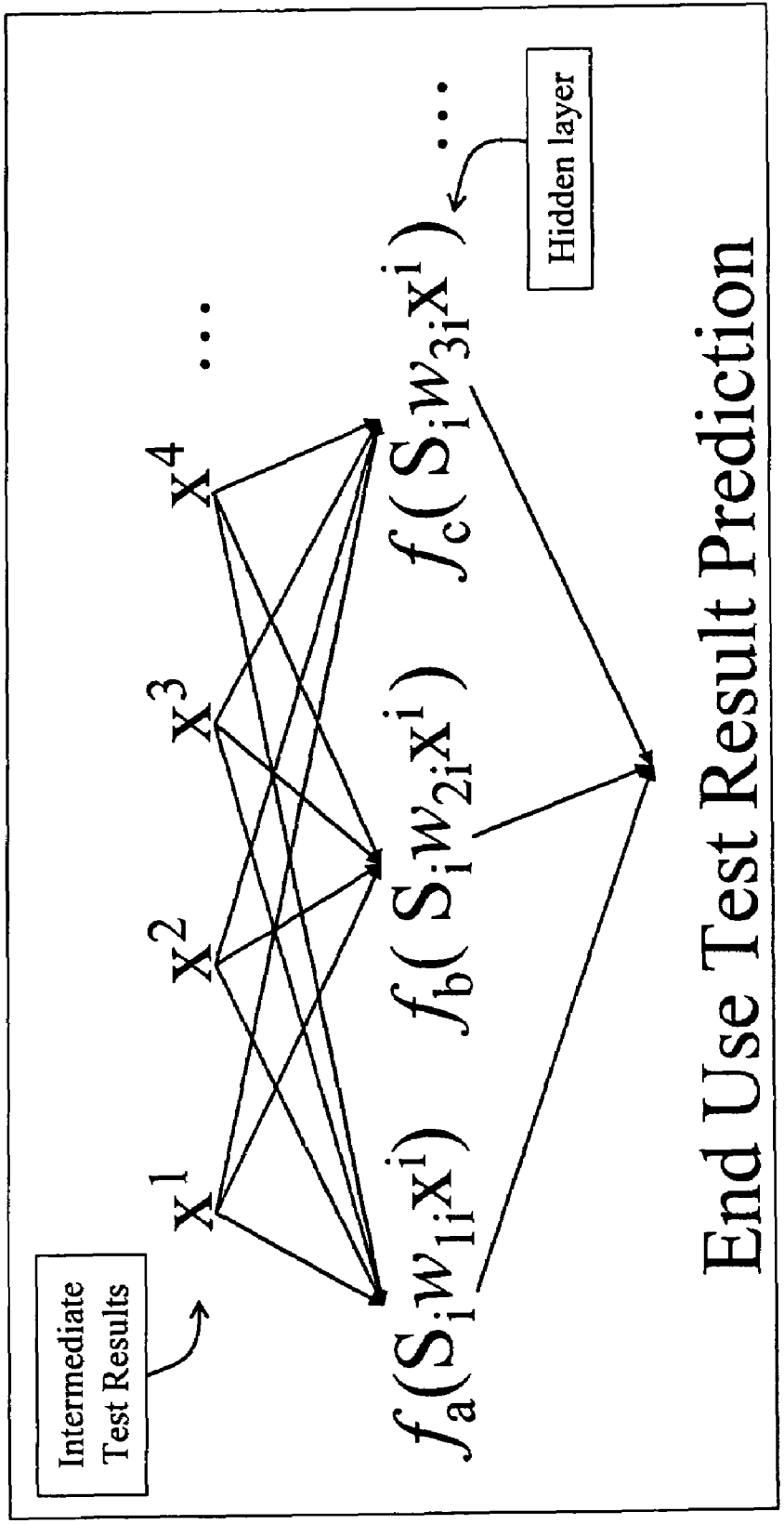
FIG. 2 is a diagram illustrating the operation of a simple neural network.

These concepts may be more fully explained by FIG. 2 which represents a simplified neural net showing one layer. This figure uses the same earlier convention where $x^n$ represents the nth Intermediate test result for a specific sample. A neural net attempts to find the values of each coefficient (a, b, c, d, etc.) that will map to the End Use Result for that Sample. While we commonly think of linear regressions (as shown in the first level), each level applies a function (for example, a sigmoid) upon each of the coefficients to produce a new set of coefficients ($w_1, w_2, w_3, w_4$, etc.). This may occur for as many layers as desired.

Once the coefficients (a, b, c, d,) are determined such that they map the Intermediate Tests Results to the Final End Use Test Result for that specific Sample to a desired degree of Error, the neural net then applies those coefficients to the Intermediate Tests results for the next Sample. If the coefficients do not map to the End Use Test for the Second Sample to an acceptable error level, then weights are applied to each coefficient and the process is repeated until coefficients are determined that produce an acceptable error level for both samples. This process is continued until a mapping function is determined that produces an acceptable level of error between all Intermediate Tests and their respective End Use Test Results.

The "information content" of the net is embodied in the set of all these weights that, together with the net structure, constitute the model generated by the net. The back-prop net has information flowing in the forward direction in the prediction mode and back-propagated error corrections in the learning mode. Such nets are organized into layers of neurons. Connections are made between neurons of adjacent layers: a neuron is connected so as to receive signals from each neuron in the immediately preceding layer, and to transmit signals to each neuron in the immediately succeeding layer.

A minimum of three layers is utilized. An input layer, as its name implies, receives input. One or more intermediate layers (also called hidden layers because they are hidden from external exposure) lie between the input layer and the output layer which communicates results externally. Additionally, a "bias" neuron supplying an invariant output is connected to each neuron in the hidden and output layers. The number of neurons used in the hidden layer depends on the number of the input and output neurons, and on the number of available training data patterns. Too few hidden neurons hinder the learning process, and too many degrade the generalizing capability of the net.

An outcome from a given input condition is generated in the following way. Signals flow only in the forward direction from input to hidden to output layers. A given set of input values is imposed on the neurons in the input layer. These neurons transform the input signals and transmit the resulting values to neurons in the hidden layer. Each neuron in the hidden layer receives a signal (modified by the weight of the corresponding connection) from each neuron in the input layer. The neurons in the hidden layer individually sum up the signals they receive together with a weighted signal from the bias neuron, transform this sum, and then transmit the result to each of the neurons in the next layer.

Ultimately, the neurons in the output layer receive weighted signals from neurons in the penultimate layer and the bias, sum the signals, and emit the transformed sums as output from the net. The net is trained by adjusting the weights in order to minimize errors. In the learning (or training) mode, the net is supplied with sets of data comprised of values of input variables and corresponding target outcomes. The weights for each connection are initially randomized. During the training process, the errors (which are the differences between the actual output from the net and the desired target outcomes) are propagated backwards (hence the name "back-propagation") through the net and are used to update the connecting weights. Repeated iterations of this operation result in a converged set of weights and a net that has been trained to identify and learn patterns (should they exist) between sets of input data and corresponding sets of target outcomes. More information concerning making and using neural nets may be found at J. Leonard & M. A. Kramer, Computers and Chemical Engineering, v. 14, #3, pp. 337-341, 1990.

Neural nets, after being trained on data, result in a correlative model that predicts a quantitative outcome when presented with a set of independent parameters as input. This quantitative result enables determination of a set of desirable input variables which maximize the performance (i.e., model outcome). This is accomplished by deploying suitable optimization techniques, viz., genetic algorithms.

Once an acceptable mapping is achieved by neural networks to estimate the function F above, a classification scheme is selected to limit the mapping function (and therefore the contours of the selected region in x space) to a particular set of mappings. For example, the uses of this invention develops a neural network model that relates families of $X_c$ vectors (wherein each $X_c$ vector represents the results of selected intermediate tests on a single Sample, sometimes known as a "calibration set" or "training set") to the corresponding engine test results. Then, future bench test screener result vectors $X_p$ (where $X_p$ is the results of the intermediate tests on a previously unknown Sample, $X_p$ is sometimes known as the "prediction set") can be tested with the neural network function F, against the $F_0$ threshold. Some will "pass", some will "fail" the neural network model.

It is possible to create a map of the pass/fail regions by using regression techniques. For example, one way of implementing this, is to "run" large numbers of simulated $X_t$ (i.e., a universe of Sample or Component Sets) vectors, then build the corresponding "pass" and "fail" regions in $X_C$ space. Those classification models would yield the same prediction results as the neural network regression model. Once F is available, it can be applied across the screener space to make contours to predict varying pass or fail results at various pass/fail criteria.

Because of the vast number of variables (Intermediate Tests) that could be employed in lubricant formulations, the inventors have found it performed to use a methodology for relevant variable selection, that will seek the best prediction of engine test performance, while optimizing the design, number, nature, and/or cost of the test screener results. While in the past it has been useful to use the formulator's experience to determine the more predictive variables, there are many mathematical techniques to also make this selection.

For data sets comprising a limited numbers of measurements (e.g., <100), an "all possible combinations (APC) of variables" approach (e.g., regressions or classifications) may be done with typical desktop computational power. These approaches typically attempt to find a fixed number of variables, e.g., n, and try the regression, or classification, in all possible combinations of the original available, measured variables. For example, if 10 screener test results are available, and a model with just 5 variables is desired, it is possible to try combinations [1 2 3 4 5], [1 2 3 4 6], [1 2 3 4 7], [1 2 3 4 10], . . . all the way until [6 7 8 9 10], for a total of 30240 regressions. In a typical 3.2 GHz Pentium 4 machine, that calculation can be completed in just 30 seconds.

For larger data sets, while it is possible to somewhat optimize the APC algorithms, there are numerous strategies to identify ideal combinations of predictive variables. For example, a forward step-wise methodology sequentially selects variables one at a time, according to their incremental classification, or prediction value. For example, if there were ten available Intermediate Tests (per sample), this method would first identify the best predictor of the ten. Next, the method would look at the remaining nine Intermediate Tests and select the next most predictive Tests, that when combined with the original selected most predictive Intermediate Test, yields the best pair of Intermediate Test predictors. The procedure is repeated until the desired number of variable, n, is selected. The number of variables may also estimated, using testing data sets, or validation procedures, do establish the best number of variables to utilize.

Another example of a methodology to identify ideal combinations of predictive variables is popularly known as genetic algorithms. In this type of algorithms, large numbers of random combinations of variables are selected, and tested for their prediction ability. Those sets showing superior predictive performance are then selected, and randomly combined, both with each other, and with other random sets. This procedure is repeated until further improvements in prediction are no longer achieved.

Genetic algorithms (GA) are robust optimizers that are able to handle non-monotonic, even discontinuous, objective functions and find global optima. The present invention's approach of coupling GA with data-driven models, viz., neural nets (NN), enables exploration of the lube composition/property space in order to identify potentially high performing regions where further experimentation may yield valuable discovery. The GA suggests input parameters (or intermediate parameters) to the neural net models(s), which in turn, predict the performance of these suggestions. Iterative feedback of these predictions to the GA lead to the "evolution" of sets of parameters that correspond to predicted performance in the desired target range.

This is more fully explained by the following prophetic example. Imagine that for a number of Samples, we have 100,000 Intermediate Tests, each with their own result of each Sample. As before, we will employ the convention that $x^n_A$ represents the $n^{th}$ Intermediate Test Result on Sample A. The GA, combined with a NN, selects pairs (or triplets or quadruplets . . . ) of Intermediate Tests and performs some manipulation upon them to create a new variable which we will designate $y^{n+m}_A$ which is equal to some $f(x^n_A, x^m_A)$, where n represents some $n^{th}$ Intermediate Tests result and m represents some $m^{th}$ Intermediate test result. If the GA uses all of the possible combination of Pairs then there would be $10^{10}$ y variables. Of course, a random selection of a smaller number of y variable could also be employed.

This new set of y variables are then fed into a neural net, as described above, to determine coefficients (a, b, c, d . . . n+m, as before) that predict the End Use Test to the desired degree of accuracy. The value of each coefficient determines which y variables are most predictive. The GA takes the most predictive and also selects some random selection of the remaining y variables. The GA then "marries" these y variables in new pair (triplet, quadruplet, etc.) combinations and produces offspring such that $z^{n+m}_A$ which is equal to some $f(y^n_A, y^m_A)$. The GA then sends these z variables to the neural net and repeats this entire process until the most predictive set of combinations of Intermediate Tests has been selected.

It is clear that the present invention is not limited to just neural network models, but may be applied to any other regression model. Furthermore, the current method has the potential of being more robust than many regression methods, as a misclassification of one, or even a handful, of results would not seriously impair the determination of the preferred regions. Moreover, the inventors note that this methodology enables models that are more parsimonious than that of regression, as it does not force preconceived function shapes to the relationship between screener tests and the engine and rig test results.

The classification model approach does not significantly limit the ability to obtain several levels of performance out of a model. The present method perceives gradations of success as well as a simple pass/fail model. Contours in the X-space of single bench test results may be developed for each desired level of performance, or a simple continuous regression model may be used to determine the contours.

Further, the present invention is not limited to linearly modeled spaces. Indeed, lubricant formulation is rife with examples of non-linear responses and therefore the method of the current invention is particularly suited to lubricant formulations. For example, even a simple wear rate analysis demonstrates the non-linear response of lubricants. In the wear rate scenario, there is a threshold level of an additive that is needed before a desired performance is reached. Below that level, there will be no or little response, and above it the desired performance level is reached. However, because of other factors, failure can occur when too high a level of the additive is in the formulation.

Figure 3:
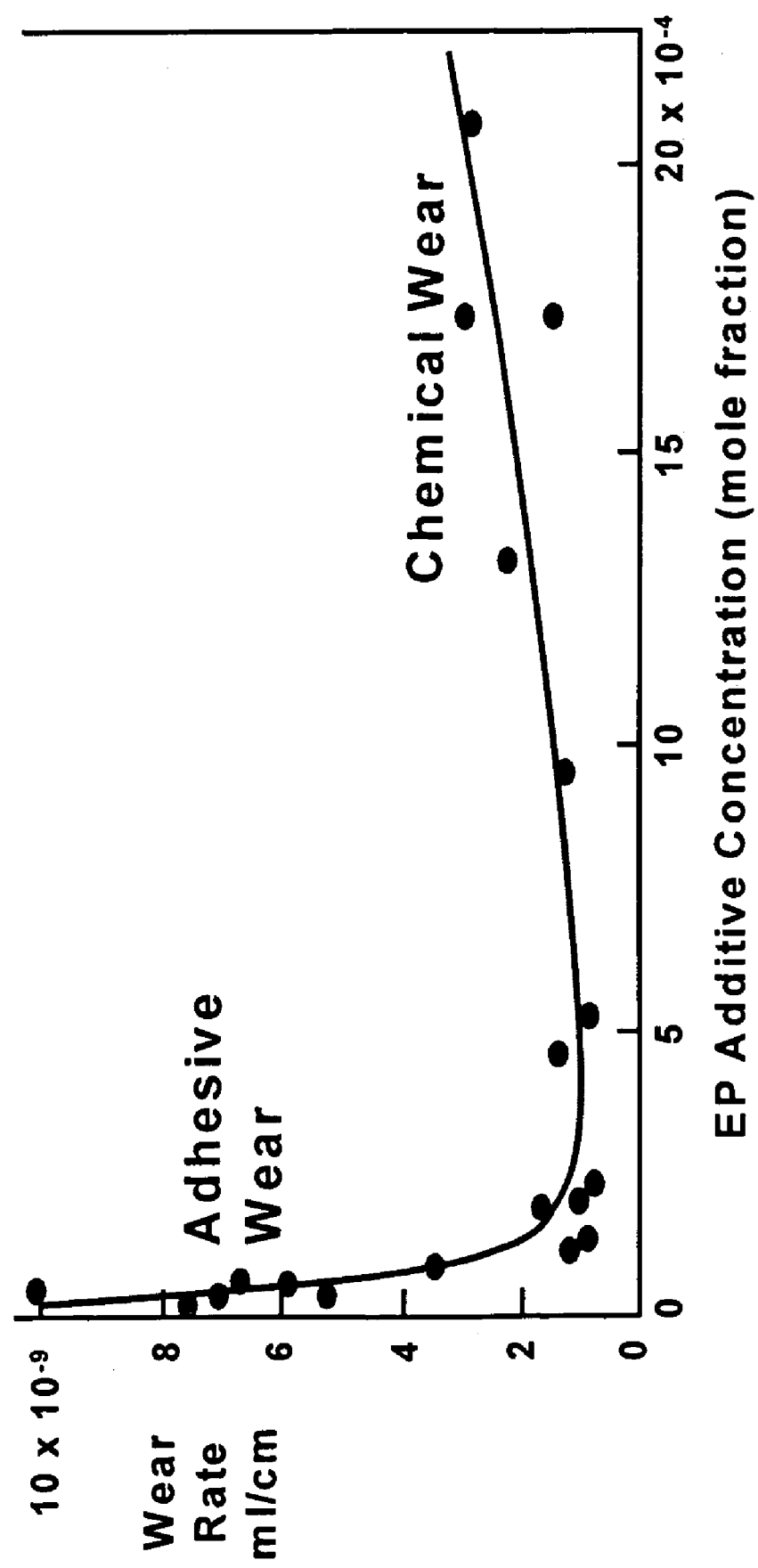
FIG. 3 is a graphical representation of the wear rate versus the amount of Extreme Pressure Additive found in one type of formulation.
Figure 4:
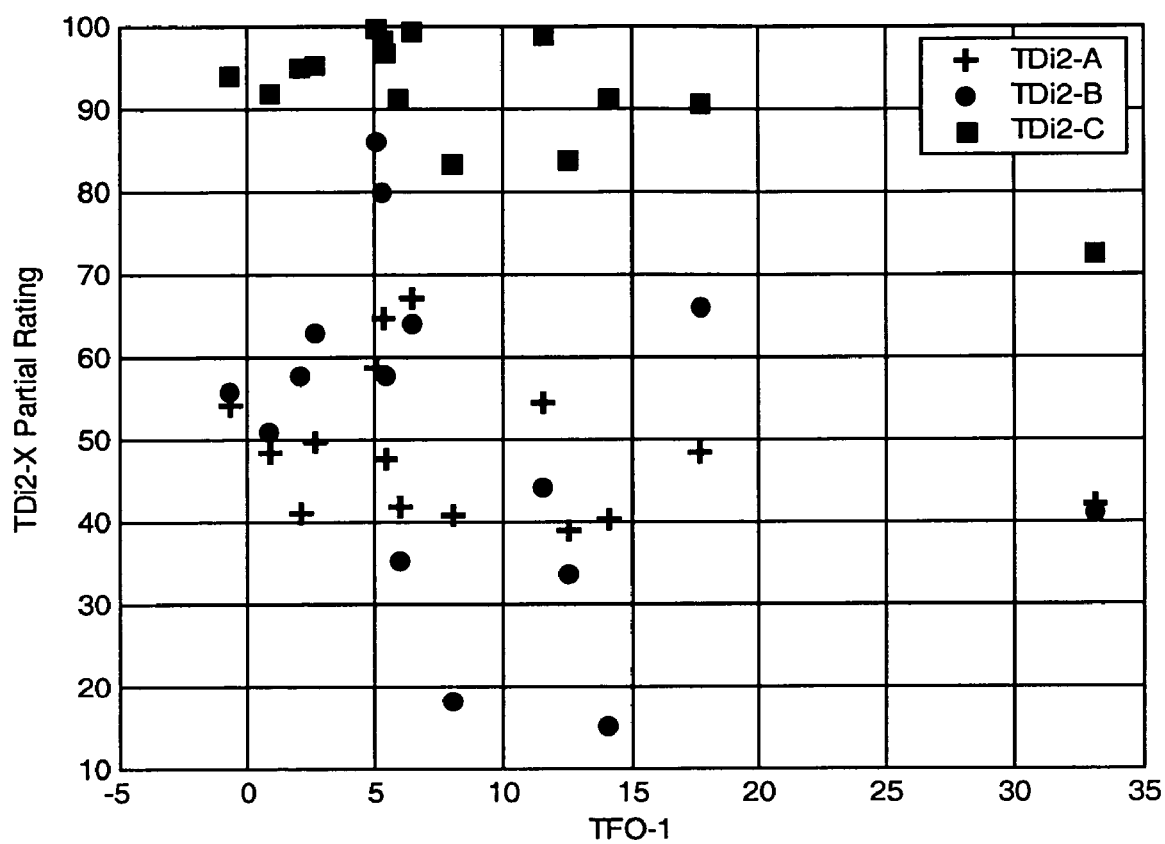
FIG. 4 through FIG. 9 are graphical representations of each Mobil thin film oxidation (tfo) test (numbers 1 through 6) plotted against the Volkswagen TDi2 (VWTDi2) test results showing no predictive ability of the individual tfo tests.
Figure 5:
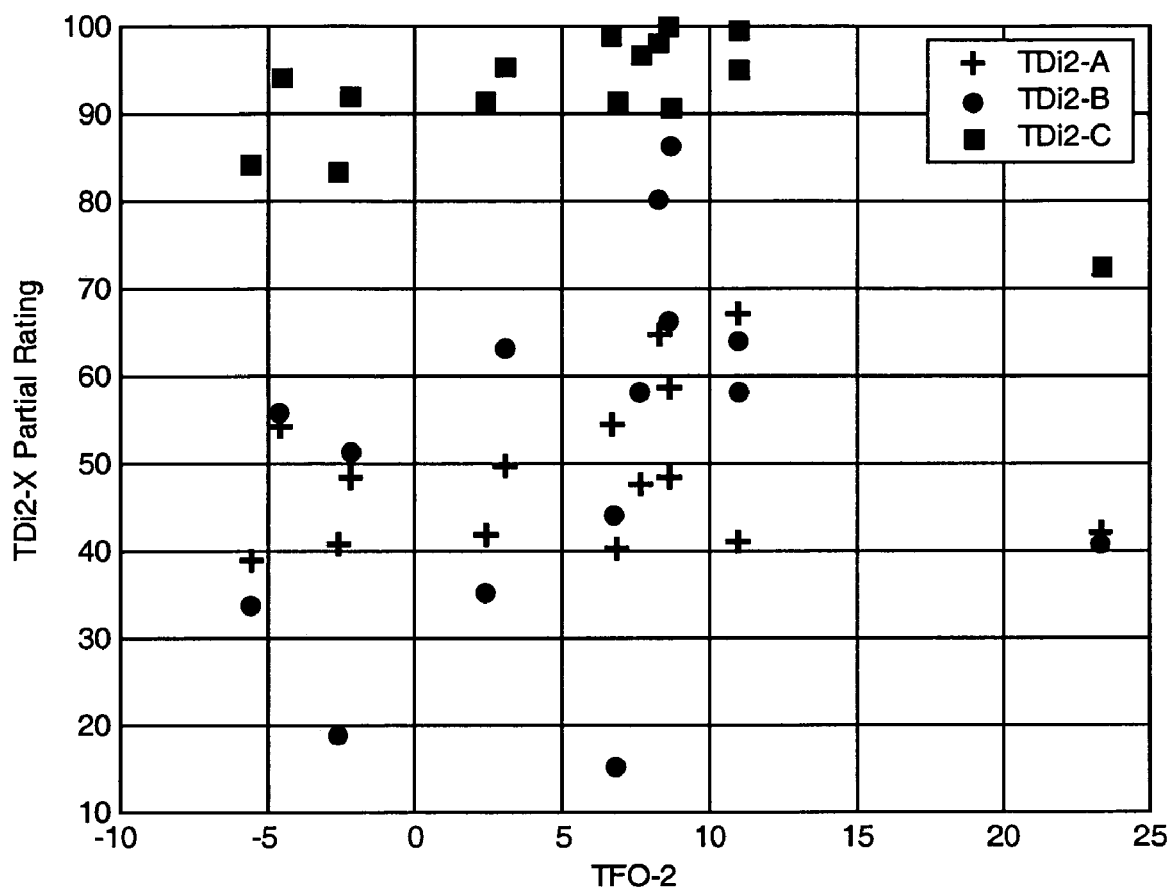
Figure 6:
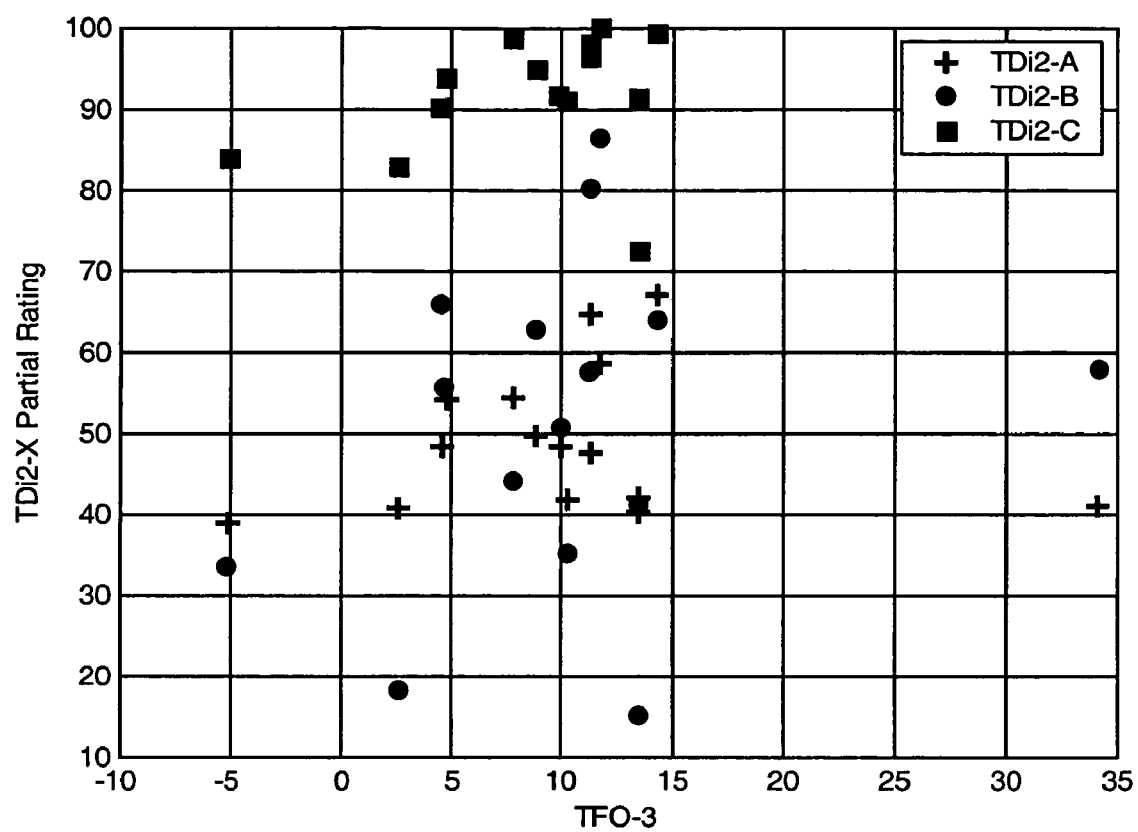
Figure 7:
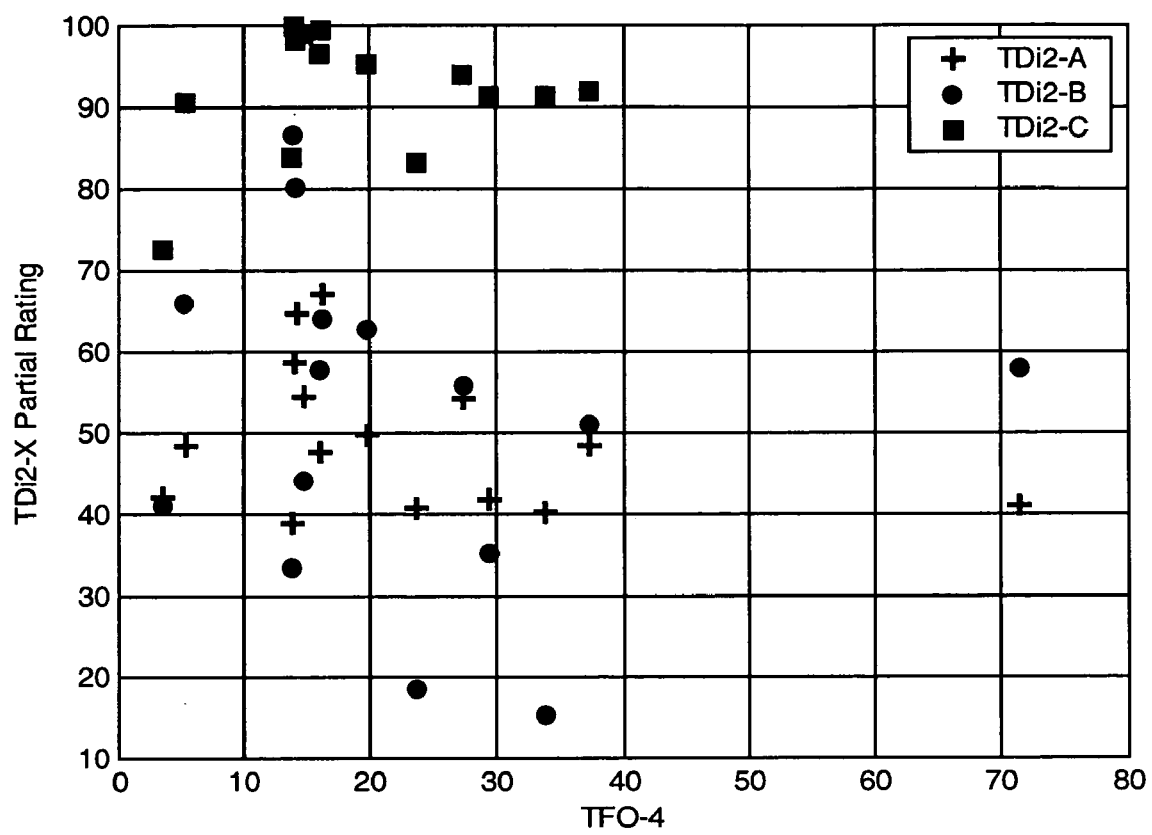
Figure 8:
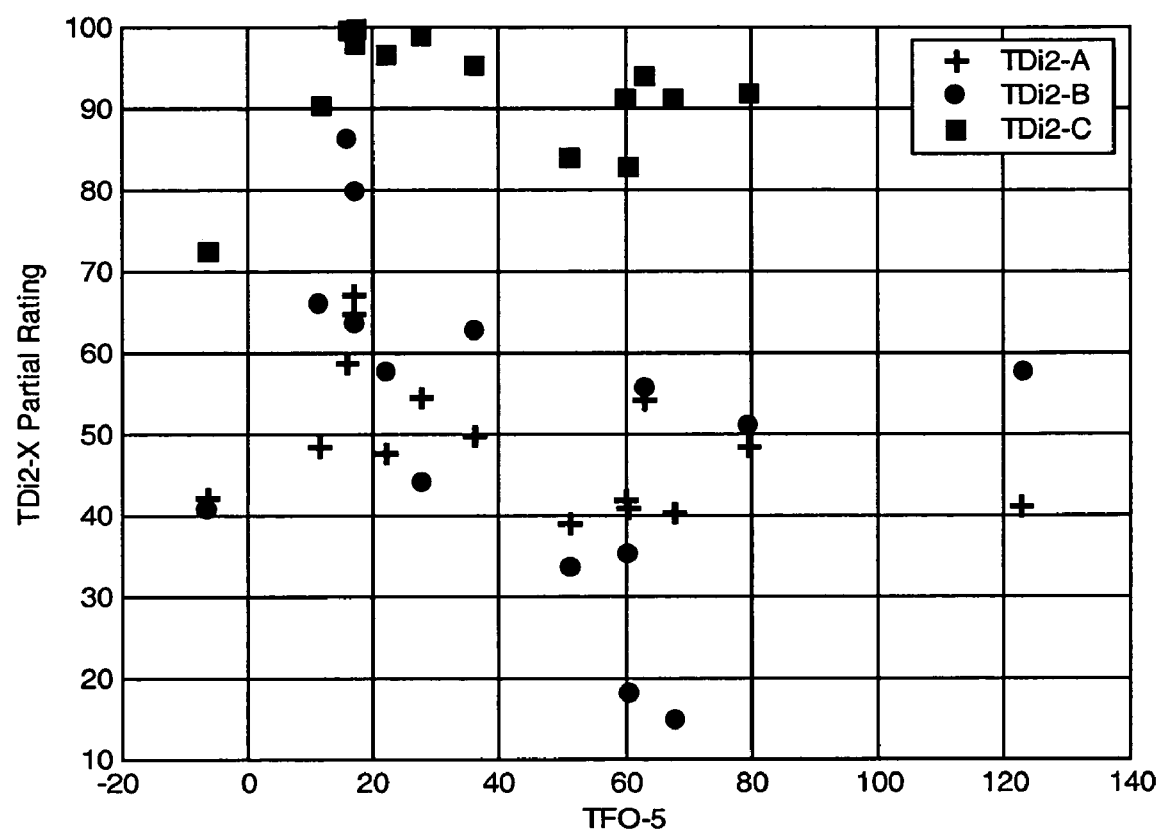
Figure 9:
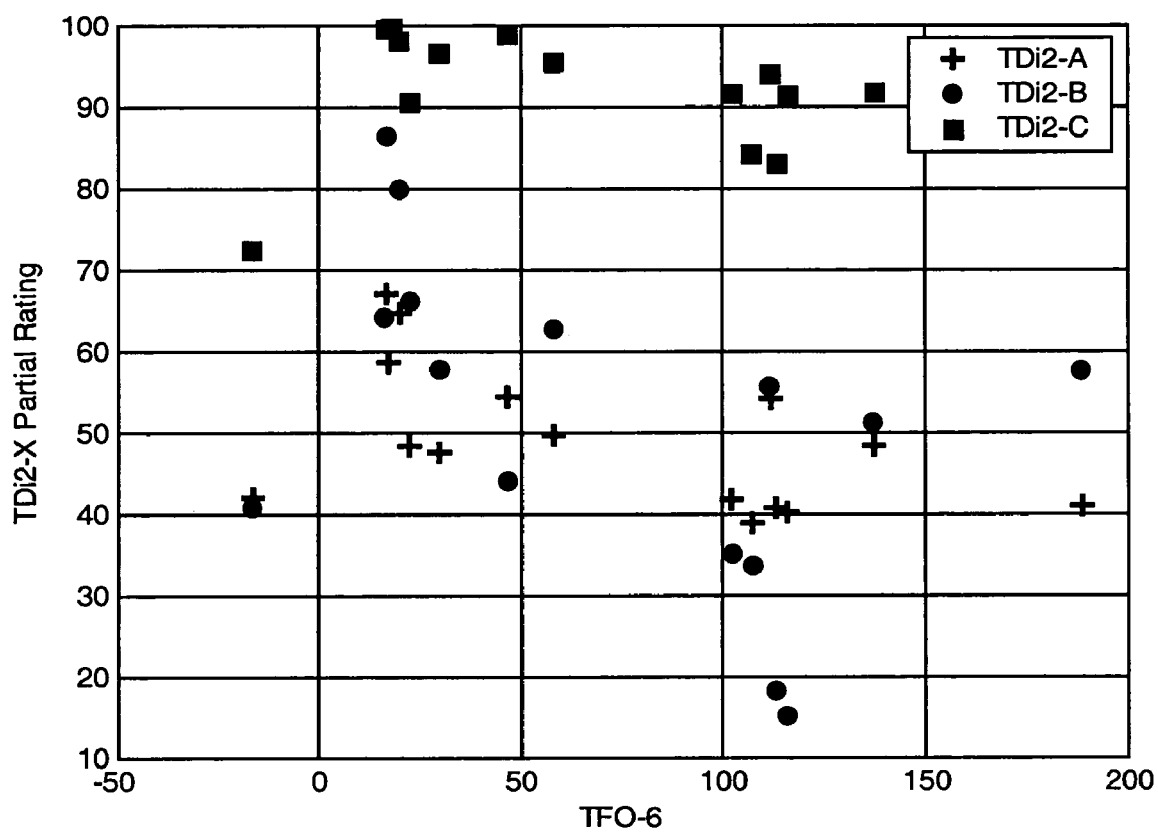

In the wear rate example shown in FIG. 3, a low wear rate is desired. At very low concentrations of the extreme pressure (EP) additive, there is significant and unacceptable wear. At high concentrations, the wear rate is unacceptable due to chemical wear. Thus, a non-linear model would be necessary to properly understand optimal additive addition to achieve the minimum wear rate.

In formulating a lubricant, the goal is to achieve optimal performance. To determine the absolute minimum in the test results shown in FIG. 3, ideally one would make multiple blends between $1 \times 10^{-4}$ to $5 \times 10^{-4}$ mole fraction and test them in multiple wear tests. This is not feasible using traditional blending and testing. However, by using methods that produce and test small amounts of a large numbers of samples, the number of blends and evaluating tests used can be greatly increased, thus being able to achieve the optimal performance level desired. Although this optimization may be performed by data mining of existing formulation databases, one particularly effective embodiment of the current invention applies high-throughput methods to create and/or test lubricant formulation samples. The introduction of these methods to lubricant research is only made feasible by the methodology of the current invention.

In one embodiment, the present invention therefore is a method to determine at least one member of the Elemental Set of Intermediate Tests which will predict End-use Test Results for lubricants which comprises:

a. Defining the members of an Elemental Set of Samples or Components having at least two members;
b. Defining the members of a set of End-use Test Results having at least two members,
   such that a first member of said Elemental Set of End-use Test Results corresponds to a first member of said Elemental Set of Samples, and
   such that a second member of said Elemental Set of End-use Test Results corresponds to a second member of said Elemental Set of Samples,
   wherein said first member of each set is not the same as said second member of each set;
c. Selecting a universe of intermediate tests that may contain appropriate members of said Elemental Set of Intermediate Tests;
d. Performing one or more of said intermediate tests upon at least two members of said Elemental Set of Samples;
e. Determining said predictive member or members of said Elemental Set of Intermediate Tests by using a predictive model;
f. Optionally, refining said predictive members of said Elemental Set of Intermediate Tests using a variable selection algorithm.

In another embodiment, the present invention is a method to determine new relationships between existing bench test data that will accurately predict End-use Test Results for lubricants, comprising:

a. Defining the members of an Elemental Set of Samples, such that each member of the Elemental Set of Samples has at least two associated members in the Elemental Set of Intermediate Tests and at least one associated member in the Elemental Set of End-use Tests.
b. Creating new members for the Elemental Set of Intermediate Tests by selecting combinations (or functional combinations) of said at least two associated members in the Elemental Set of Intermediate Tests which correspond to a specific member of said Elemental Set of Samples.
c. On at least two of said newly created members of Elemental Set of Intermediate Tests, use a predictive model to determine the most predictive member(s) of the Elemental Set of Intermediate Tests.
d. Optionally, refining the members (or relationship of the members) of the Elemental Set of Intermediate Tests using a variable selection algorithm.

This embodiment of the current invention is illustrated by the following Example.

EXAMPLE 1

Various bench tests, known as the Mobil Thin-Film Oxidation Tests ("tfo"), were conducted on various lubricant samples. The test was developed to permit the study of controlled oxidation and deposit formation under high temperature, short contact time conditions. The test oil is subjected to oxidizing conditions as a thin dynamic film passing over a rotating aluminum disk, which is maintained at an elevated test temperature while air is passed over the surface of the oil film.

The test oil is circulated continuously from a reservoir by a gear pump through a delivery tube to the center of a conical-faced disk. An electrical heating element inside the delivery tube is generally used to raise the temperature of the test oil to 300° C. to permit precise control of the temperature at the disk surface. The disk is heated by a ceramic heater mounted behind it. A thermo-couple is embedded immediately beneath the surface of the disk to provide read-out and input signal to a temperature controller. Typically, disk temperature is set in the range from about 315 to 360° C. The disk is rotated at 2500 RPM, which generates a thin oil film across the surface of the disk. As the oil is spun off the disk, it is caught by a water-cooled collector, which quenches the oxidation reaction. The oil is then returned to the reservoir. An excess of air is supplied to the surface of the oil film through a line and an air pump. The air supply is purified by a series of adsorbents before entering the reaction zone. A further description of the testing are described in SAE (Society of Automotive Engineers) Technical Paper 851797, "Development of a High Temperature Jet Engine Oil—Laboratory and Field Evaluation", available at on-line at http://www.sac.org/technical/papers/851797.

For grading, the disks are radially divided into 6 equal sections and then each section is visually assigned a rating.

Thus, the tfo1 test is the rating for the innermost section, the tfo2 is for the next outer band, etc. Each band is provided a visual rating from 0 to 100, with 100 being the cleanest. A visual rating of 0 would indicate heavy black deposits. A rating of 25 would be given to an area that exhibited medium-dense opaque brown or black deposits. A rating of 50 would be given to indicate semi-transparent brown deposits. A rating of 75 indicates transparent yellow-brown deposit. A rating of 100 indicates a clean, shiny surface. Ratings may be interpolated as necessary to capture a correct visual picture of the rated area. If a rated area exhibits more than one rating, a weighted average, corresponding to the percentage surface area at each rating, should be taken.

For this example, the Volkswagen GTI End-use test ("VWTDi2 engine test") was also performed upon each lubricant sample. The Volkswagen GTI End-use test is described in CEC (Coordinating European Counsel) Publication L78-T-99. While far too lengthy to describe in this disclosure, one of ordinary skill in the art recognizes that the present invention does not rely upon this specific End Use Test, but upon any End Use Test that the person wishes to model.

As can be seen from the graphs of FIGS. 4 to 9, none of these six bench tests demonstrated any ability to predict the results of the VWTDi2 engine test. Employing the above embodiment of the present invention, the inventors created a universe of Intermediate Tests by creating a series of two-dimensional pairings of the bench tests. Thus, 30 three-dimensional plots were developed consisting of the results of a first bench test on the X-axis, a second bench test on the Y-Axis, and the results of the VWTDi2 engine test on the Z-Axis. For example, for the first of the set of Intermediate Tests, the results of the tfo1 test were plotted against the results of the tfo2 test and the VWTDi2 engine test. Likewise for the second of the set of Intermediate Tests, the results of the tfo1 test were plotted against the results of the tfo3 test and the VWTDi2 engine test. This was continued until all possible two-space combinations were created.

The inventors then modeled each of a set of Intermediate Tests (and combinations thereof), using a Linear Discriminate Analysis Cluster Method, to determine which test(s), or combination of tests, exhibited the best predictive ability to the End-use qualifying Test. The inventors were quite surprised to find that a combination of two intermediate tests, tfo1 and tfo5, each non-predictive by itself, was predictive in their combination.

Figure 10:
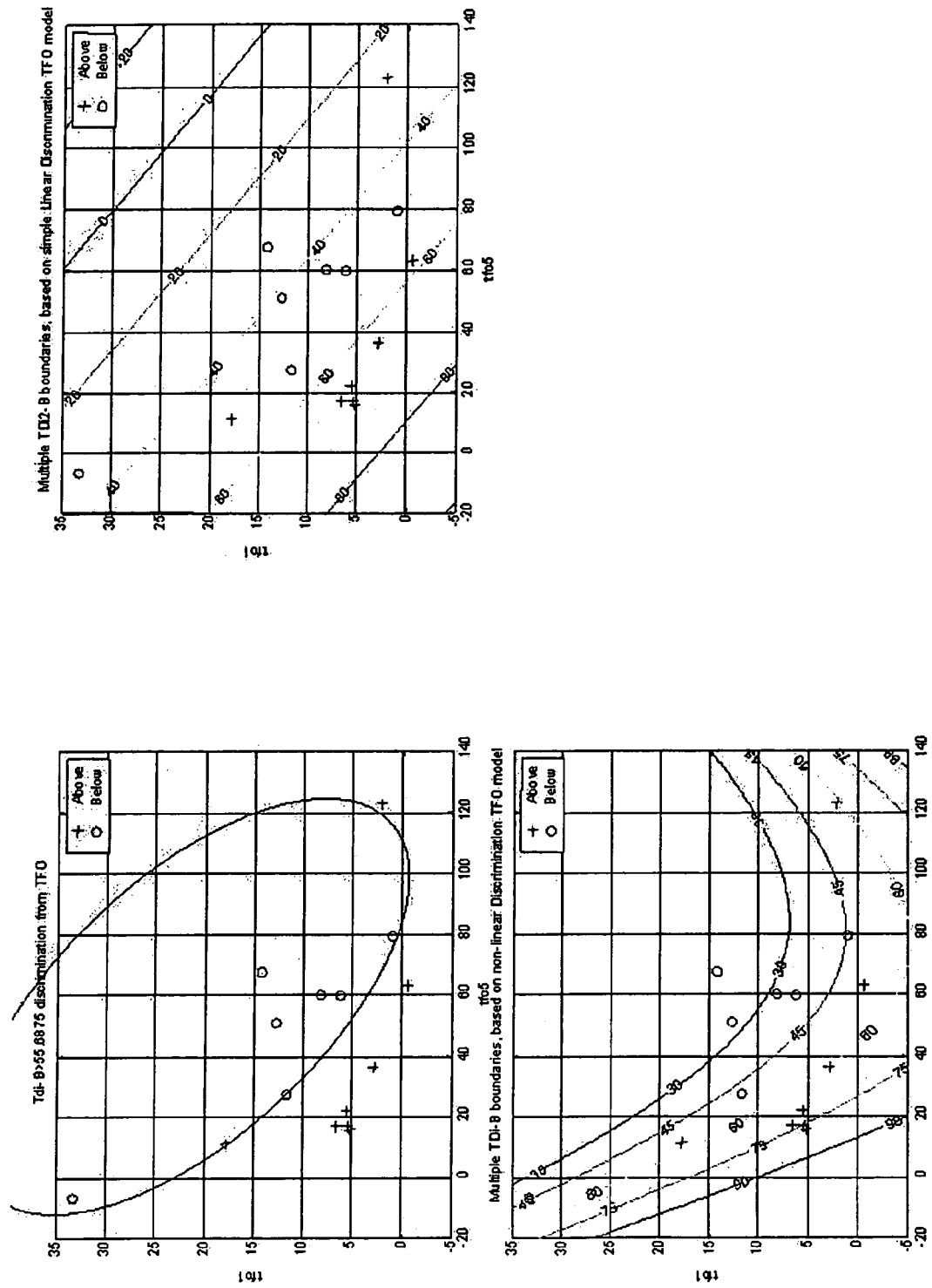
FIG. 10 presents three graphical representations of the tfo1 vs. the tfo5 test vs. the VWTDi2 test (on the z-axis). Each individual graph has overlays showing the predictive models provided by either linear or non-linear correlation functions.

FIG. 10 illustrates this case. This graph provides three representations of the tfo1 test (plotted on the x-axis) vs. the tfo5 test (plotted on the y-axis), each data point indicating whether the VWTdi2 test was passed or failed. Each individual graph has an overlay showing the predictive correlations using linear and non-linear predictive models. As can easily be seen by the ellipses of the first graph, the model has predicted a two-dimensional space of the tfo1 and tfo5 bench tests that is predictive of passing the VWTDi2 engine test. Thus, while none of the bench tests was individually predictive, in a simple two-dimensional combination, these bench tests were predictive. Moreover, graphs two and three of this figure demonstrate a linear and non-linear predictive technique further refining the accuracy of the combined tfo1 and tfo5 predictive model.

One of ordinary skill in the art realizes that these combinations that form the universe of members of the Elemental Set of Intermediate Tests need not be one-to-one, or indeed even linear. Also it is clear that these combinations do not have to be limited to a simple 3 dimensional space, but can encompass up to an n+m−1 dimensional space where n represents the number of original bench tests and m represents the original number of end-use qualifying tests. Thus, in this case, there are 6 original intermediate tests (tfo1 to tfo6) and one original end-use qualifying test (the VWTDi2 engine test) allows for a maximum of a 6dimensional space (5 bench tests and the VWTDi2 engine test) for modeling.

EXAMPLE 2

This method of the current invention as described in paragraph [0064] is illustrated by the following example. The inventors employed the described inventive methods to determine a formulation's component sensitivity toward the results of the same WTDi2 engine test as described in the previous example. The results from the VWTDi2 engine test were chosen as the Elemental Set of End-use Results because the inventors had access to a database with a sizable number of test results.

To determine a proper Elemental Set of Samples and the Elemental Set of Intermediate Tests, the inventors began with their knowledge that the control of sludge, varnish and deposits formation were considered instrumental in passing the VW TDi2 test. Because of this relation, the inventors determined two separate Elemental Sets of Samples—a fresh oil set and an aged Catalytic Oxidation Test oil set (which corresponded to the fresh oil set, but had been oxidized by the Catalytic Oxidation Test as described in U.S. Pat. No. 3,682,980, which is hereby incorporated by reference). Both of these Elemental Sets of Samples would point to the same Elemental Set of End-Use Results, thus allowing for a unique set of Intermediate Tests to be developed for each of the Elemental Set of Samples.

To determine a possible universe of Intermediate Tests for the Catalytic Oxidation Test aged oil Sample set, the inventors employed two methods. First, the inventors relied on their knowledge of sludge, varnish and deposit formation in lubricant oil samples and the additives and base stocks that effect the formation of sludge, varnish and deposits. Second, the inventors examined the relationship between the input sample sets and engine test performance.

Figure 11:
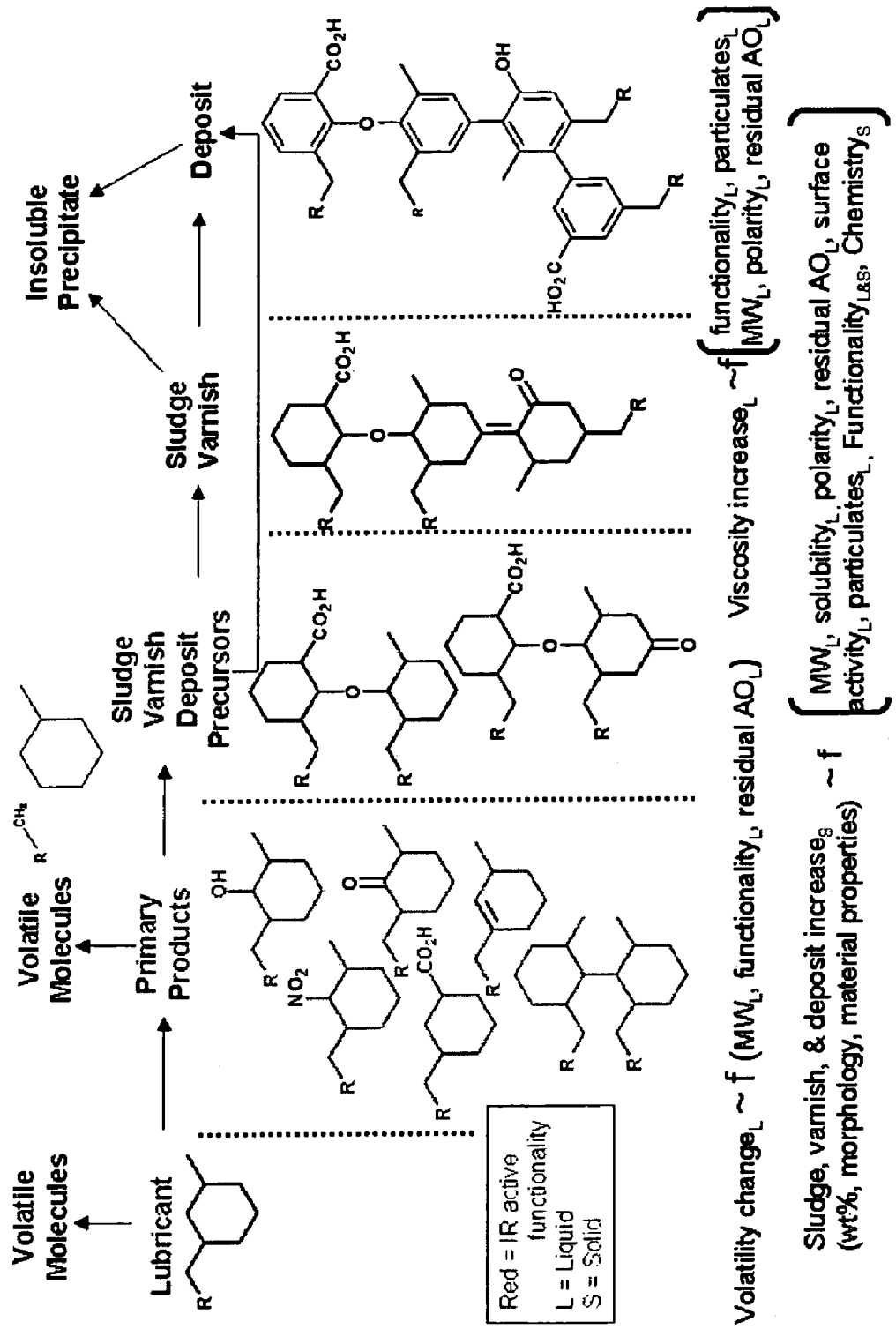
FIG. 11 is a representation of a mechanistic model for the formation of sludge, varnish and deposit formation in lubricants.

Sludge, varnish and deposits can be considered to be an extension of oxidation and along with viscosity and volatility changes are a consequence of the molecular changes that occur in the lube as it is subjected to heat, oxygen, combustion and the engine environment in general. The inventors considered from the literature possible mechanisms of the molecular changes expected to occur in the formation of sludge, varnish and deposits. Reviewing the literature, the inventors developed a suggested mechanistic model for the formation of sludge, varnish and deposits. FIG. 11 depicts this mechanistic model. Using this model, the inventors identified molecular level measurements needed as indicators of volatility, viscosity increase and the formation of sludge, varnish and deposits to be an extension of oxidation, and along with viscosity and volatility changes are a consequence of the molecular changes that occur in the lube as it is subject to heat, oxygen, combustion and the engine environment in general.

The mechanism shown in FIG. 11 demonstrates how certain functionalities (oxygen, nitrogen and unsaturation) are added to the lubricant molecule resulting in a change in its molecular weight. At the same time, the antioxidants in the lubricant are being depleted. The combination of these two factors results in changes in polarity, particulate content, solubility, surface activity and chemistry of the lubricant. The mechanism serves as the basis to identify a set of Intermediate Tests that are predictive of the End-use Test Results, which are listed in Table 1.

These tests were run on 21 samples, and the results are provided in Table 2. Neural net models were developed using the methods set out by J. Leonard & M. A. Kramer, Computers and Chemical Engineering, v. 14, #3, pp. 337-341, 1990, combined with the following cross-validation methodology. As there were 22 samples for which engine performance data were available, 22 different models (constructed with identical architecture) were developed for each of the two cases, i.e., for used and fresh oil properties, using 21 data points (One sample was not included in each run) for training each model and validating each model with the remaining datum. The training process for each of these models was terminated when the prediction error on the validation datum was minimized. The final models were then trained on all 22 data, to ensure that the training process did not extend beyond the point where the convergence exceeded the level dictated by the average validation error. This final process prevents overfitting the data.

Using these neural nets, a predicted value for the VW TDi2 tests was developed for each member of the sample set. As one of ordinary skill in the art knows, the actual neural net is a remarkably complex set of code instructions that cannot be easily reproduced here. However, using the techniques of the above paragraph on the data supplied in Table 2, the same neural nets may be developed.

From these neural nets, these inventors realized that two separate groupings of the original Sample Elemental Set could be predictive of the VW TDi2 end-use test result: a fresh oil group and a Catalytic Oxidation Test aged oil group. In the fresh oil group, the neural net identified the parameters of the amount of calcium and magnesium detergent, DPA (alkylated diphenyl amine) antioxidant measured in an IR spectrum at 1600 cm−1, and dispersant measured in an IR spectrum at 1230 cm−1 as predictive. In the Catalytic Oxidation Test aged oil group, the neural net identified the parameters of the change in the Total Acid Number (TAN), the saturation, the Aromatic content and the Polar content of the Catalytic Oxidation Test aged oil.

Figure 12:
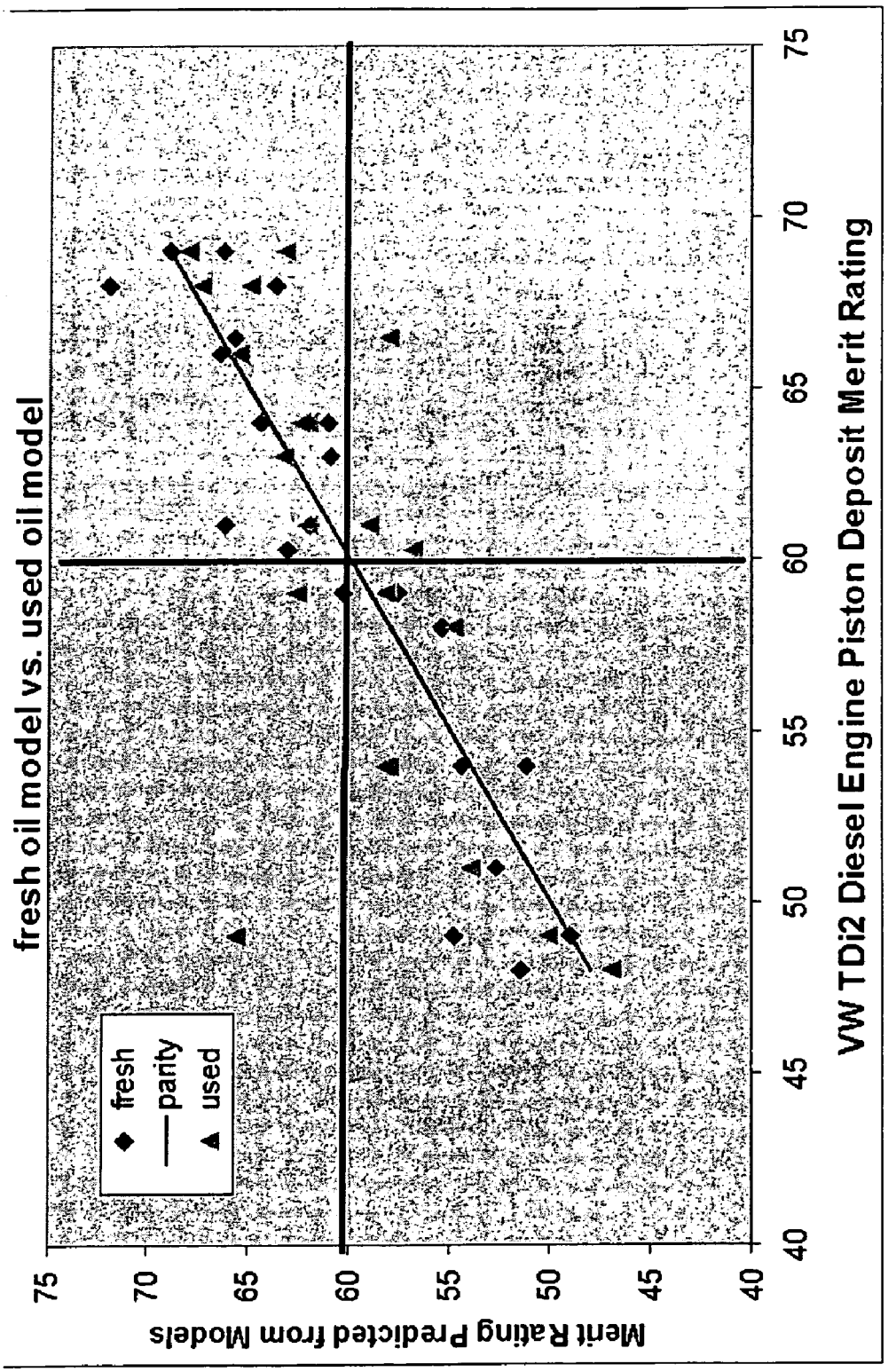
FIG. 12 graphically depicts the predictive capability of the fresh-oil and Catalytic Oxidation Test aged oil models to the VWTDi2 End-use test.

The actual VW TDi2 test result for each sample was collected and is presented as Table 3. These actual test results were compared to the predicted values for both the fresh oil and Catalytic Oxidation Test aged oil groups. FIG. 12 demonstrates that both neural net models (the predicted values for the fresh and Catalytic Oxidation Test aged oil sets) accurately predict the pass/fail parameters of the actual VW TDi2 engine test data. Specifically, this figure shows that for the fresh oil model, the neural net equations correctly predicted a pass or failure (a value of greater than or less than 60, respectively). This figure also demonstrates that the Catalytic Oxidation Test aged oil neural net model was almost as good, making a correct prediction 75% of the time. As can be seen from this example, once the Elemental Set of Intermediate Tests is established and correlated to the End-use qualifying test results, the present invention allows one to accurately test unknown samples to determine their ability to pass the End-use qualifying tests.

In another embodiment of the present invention, a subset of the members of the End-use qualifying data may be used to establish the members of the Elemental Set of Intermediate Tests. Once those members are established to the desired level of confidence, the remainder of the subset of End-use qualifying test results could be used to predict components of the members of the Elemental Set of Samples. Component predictions could be made because the different portions of the Elemental Set of Intermediate Tests would become important by differentiating between the End-use members. This method comprises:

1. Defining the members of the Elemental Set of Intermediate Tests using a subset of members of the Elemental Set of End-use test results as per the method of paragraph [0053].
2. Defining the members of a subset of the Elemental Set of End-use test results that were not used to establish the members of the Elemental Set of Intermediate Tests.
3. Using a predictive model on at least two members of the Elemental Set of Intermediate Tests and at least two members of the unused subset of the Elemental Set of End-use results to determine the more predictive members of the Elemental Set of Intermediate tests.
4. Optionally, refining the members of the Elemental Set of Intermediate Tests using a variable selection algorithm.

EXAMPLE 3

Divide the members of the Elemental Set of End-use test results into at least two subsets. The first subset would include all members in which the End-use qualifying test was barely passed. The second set would include all members in which the End-use qualifying test was strongly passed. Intermediate subsets could be created if so desired. Using the members of the Elemental Set of Intermediate Tests as described in the above method, determine which samples (or which components of which samples) would be associated with each subset. The components or mixture of components, selected by the genetic algorithms would establish the relationship between components of samples which permit the End-use qualifying tests to be passed.

EXAMPLE 4

Using the data generated in Example 2, in this example, the inventors analyzes the IR spectra to find recurring sharp spikes or ranges that were predictive of either passing or failing the tests. The inventors then would search to find what other components would exhibit the same spikes or ranges in those intermediate tests. New lubricant formulations are then prepared with those identified components and tested with the Intermediate tests to verify the efficacy in predicting the End-use tests results. Finally, the inventors perform End-use tests to verify the efficiency of the new, "out of the box", components added to the formulation.

Another embodiment of the present invention is a method for determining the relationship between a set of Intermediate tests and a set of End-use tests for lubricant samples comprising:

1. For each sample, a means for producing results from at least two tests selected from the group consisting of:
   i. Wear Resistance
   ii. Friction Reduction
   iii. Thermal Stability
   iv. Oxidative Stability
   v. Elastomer Compatibility
   vi. Viscosity
   vii. Volatility
   viii. Corrosion Resistance
   ix. Metal Passivation
   x. Miscibility
   xi. Visual Appearance
   xii. Chemical Composition
   xiii. Acidity
   xiv. Total Base Number (TBN)
   xv. Total Acid Number (TAN)
   xvi. Deposit Forming Tendencies;

2. At least one End-use test result corresponding to each of said samples;
3. An analyzer employing predictive models wherein said predictive model determines said relationship between said Intermediate tests and said End-use test or tests;
4. Optionally, a set of algorithms to determine the composition or components of additional formulated samples determined by backfitting unknown samples or components that correspond to the results of the most predictive Intermediate tests.

Figure 13:
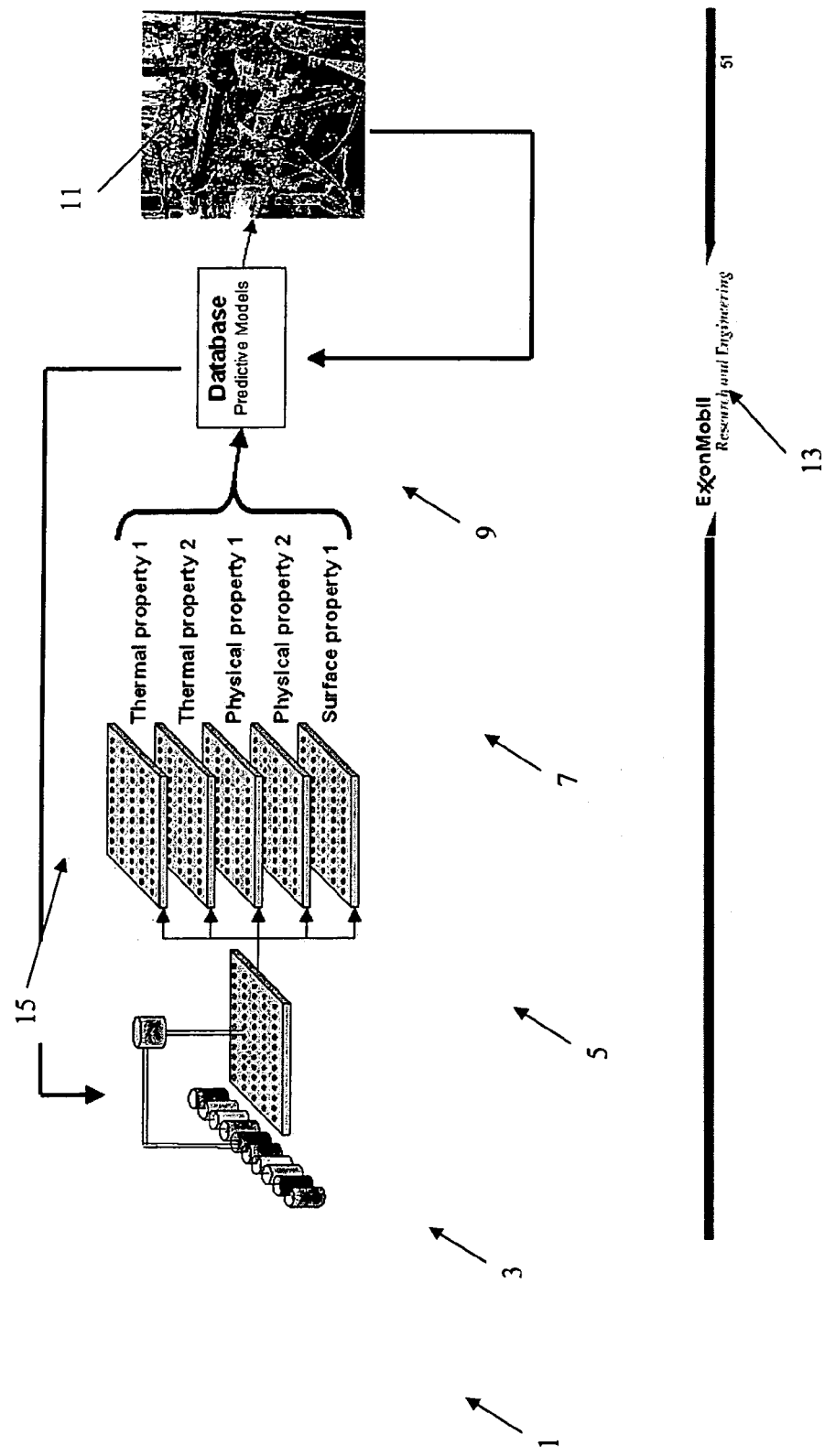
FIG. 13 is a component drawing demonstrating the interconnection of many of the derived intermediate tests in a single apparatus.

FIG. 13 details one possible non-limiting form of this embodiment. Components (1) are combined at a blending station (3) to create an Elemental Set of Samples. While the invention allows for any number of candidate samples (greater than one) to be produced, FIG. 13 represents a two-dimensional array of 60 samples. Sample sizes, if desired, may vary as appropriate for the test to be performed. As shown in the figure, more than one array may be produced. Each array is then subjected to at least one test from the Elemental Set of Intermediate Tests (5) which produces results (7) corresponding to each sample. Such testing may occur simultaneously (in parallel) or in sequence. While the current embodiment anticipates the desirability of a mechanical means to transfer the samples between tests, any means, including manual, may be employed. Standard and non-limiting members of the Elemental Set of Intermediate Tests for this embodiment may include for example oxidation tests, functionality (Carbonyl) formation, residual antioxidancy and stability tests, molecular weight, Chemical Fraction Analysis (GPC) tests, Noack Volatility as determined by Mass Spectrometry (MS), Thermal Gravimetric Analysis (TGA) and Purge and Trap Gas Chromatography (P&T GC), Iatroscan to determine the polar fraction of the molecules, viscosity tests and UV-VIS tests to determine aromatics concentration, color and turbidity. Other tests could also include TAN, TBN, seal swell tests, metal and copper corrosion tests, rust inhibition, antiwear, and elemental analysis tests.

The results (7) are placed in a database or data storage device (9) which either does or will contain the results of the Elemental Set of End-use Tests (11). In this embodiment, the database (9) also contains predictive models that determine the predictive efficacy of each test in the Elemental Set of Intermediate Tests (5) through a feedback process (13). The predictive models employed may be any of those herein discussed or any known to one of ordinary skill in the art. However, one of ordinary skill in the art may easily see that the software to perform the predictive models may be separated from the database or indeed each model may be performed in a different and separate manner from the next.

The embodiment in FIG. 13 also includes an option feedback loop (15) which represents the additional genetic algorithms that could be used to predict unusual or unknown members of the Sample Elemental set as described in Example 4.

Tests known to be useful as members of the Elemental Set of Intermediate Tests are described below, but are in no way limit the set of possible tests useful as members of the Elemental Set of Intermediate Tests.

Antioxidancy and Oxidative Stability

Lubricants must exhibit good antioxidancy properties. As lubricants age in engines, industrial equipment and bench test equipment, reactive species are generated such as radicals, hydroperoxides, and organic nitrates. These reactive species cause the lubricant to oxidize (form oxidation products) and degrade in performance over time. The capacity of a lube to resist oxidation is called antioxidancy or oxidative stability. Reactions involving radicals are the most difficult to control.

The lubricant's capacity to control radical chemistry is a type of antioxidancy or oxidative stability that is measured by the High Pressure Differential Scanning Calorimetry test (HPDSC). This test essentially measures the amount of antioxidancy or oxidative stability an oil has for controlling the build up of free radicals and thus slowing oxidation. Hydroperoxides and organic nitrates also cause oxidation but they react much differently with the lube than radicals. The lubricant's capacity to control hydroperoxide and organic nitrate chemistry is the second type of antioxidancy or oxidative stability and it is different than the lubricant's capacity to control radicals. Antioxidants that control radicals, hydroperoxides and organic nitrates are all different in their chemistry.

In conventional lubricant bench tests, antioxidancy is measured by ASTM tests such as D943, D2272, D2070, D2893, D4636, D5846, and D6514. These tests do not discriminate between radical control or hydroperoxide and organic nitrate control. Nor do these tests follow the evolution of basic oxidation products. Therefore it is difficult to make adjustments in lubricant chemistry to compensate for lack of antioxidancy or oxidative stability when the type of chemistry required is not known.

The inventors have found that antioxidancy or the oxidative stability of a lubricant may be determined in a high through-put environment using methods such as FTIR, PDSC, and TGA. Including these methods within the scope of this invention provides techniques for a formulator to employ HTE techniques to quickly evaluate multiple formulations.

Oxidative stability or residual antioxidancy is normally measured by tests such as ASTM tests D943, D2272, D2070, D2893, D4636, D5846, and D6514. The inventors have found that oxidative stability may be determined in a high through-put environment using GC/MS to measure the degradation rates of cumene hyperoxide ("CHP") and ethylhexyl nitrate ("EHN"). These degradation rates directly correlate to the oxidative stability of a lubricant. Including this method in the current invention provides one embodiment for a formulator to employ HTE techniques to quickly evaluate multiple formulations.

Chemical Fraction Analysis (GPC)

The chemical makeup of the base oil lubricant is critical to the function of that lubricant. Because of this, several methods have been used to determine the fraction of naphthenes ($C_N$), aromatics ($C_A$) and saturates ($C_P$) in the base oil of the lubricant. These fractions may be determined by measuring the polar fractions (polarity) of the various molecular types present in the lubricants. Polarity is also important as it provides another measure of the oxidative stability of the lubricant. Formulators currently measure polarity using tests such as ASTM test methods D3328 and D3524. These tests are also designed to separate volatile components, and therefore are not amenable to the higher molecular weight nonvolatile fractions. The ASTM D4124 test can separate the higher molecular weight nonvolatile fractions, but the test was designed specifically for separating asphalts into four chemically distinct fractions. Also miniaturized techniques such as HPLC still are inconvenient for HTE because they take hours to perform.

The inventors have found a method of determining the polar fractions of a lubricant by the use of Iatroscan thin layer chromatography. The Iatroscan of lubricants is particularly adapted to HTE applications as it can be accomplished in minutes. Including this method in this invention provides one method for a formulator to employ HTE techniques to quickly evaluate multiple formulations and provide advantages over the other methods discussed previously for measuring polarity.

Friction Reduction and Wear Resistance

The ability to reduce friction and resist wear is a primary function of a lubricant. Formulators currently measure wear resistance and friction reduction using tests such as ASTM test methods D2670, D2783, D3702, D4172, D4304, D5183, D5302, D5707, D5968, D6425, and D5620. The inventors have found that both wear resistance and friction reduction can be measured in a HTE environment using nano and micro indenter techniques. Including these methods in the current invention provides one embodiment for a formulator to employ HTE techniques to quickly evaluate multiple formulations.

Additional Lubricant Properties

Formulators are also concerned about making high throughput measurements of sludge, varnish and deposit formation, insolubles, sediment, TAN, TBN, chemical analysis, seal swell and the corrosivity of metals. Formulators currently measure sludge, varnish and deposit formation using ASTM tests such as D5302, and D4859. Miscibility, insolubles and sediment measurements are made using ASTM measurements such as D893, D6560, and D2273. TAN and TBN are measured using ASTM tests such as D94, D664, D5770, and D5984. Chemical analysis measurements are made using tests such as ASTM tests D5291, D2622, D5185. Seal swell is measured using tests such as ASTM test D4289. Similarly, Critical Metal and Copper Corrosion and Rust inhibition tests are conducted in accordance with tests such as ASTM D2649, D4636, D5968, D5969, D6547, D6557 and D6594.

NOACK Volatility

Those skilled in the art recognize that the NOACK volatility of a lubricant has become a key measure of expected engine performance. Formulators currently measure NOACK volatility and volatility in general by using ASTM tests such as D2715, D5291 and D5800. However, the inventors have discovered a method to determine the NOACK volatility using Purge and Trap Gas Chromatography (P&T GC), Thermal Gravimetric Analysis (TGA) and Mass Spectrometry (MS). Including this method in the current invention provides one embodiment for a formulator to employ HTE techniques to quickly evaluate multiple formulations.

Color and Turbidity

After stressing a lubricant, the color and turbidity of a lubricant are important predictors of final lubricant performance. Color is determined by ASTM test D1500. Including these methods in the current invention provides one embodiment for a formulator to employ HTE techniques to quickly evaluate multiple formulations.

Other Properties

Some properties, such as viscosity, have previously been successfully miniaturized and made high throughput. Typical ASTM tests used to measure viscosity are: D2270, D445, D2422, D2532, D2983, D5133, D5763, D6022 and D6821.

What is claimed is:

1. A method to determine which members, individually or in combination, of an Elemental Set of Intermediate Tests are predictive of an Elemental Set of End-Use Test Results, the method comprising:

providing an Elemental Set of Samples having at least a first member and a second member;

providing an Elemental Set of End-Use Test Results for said Elemental Set of Samples, the Elemental Set of End-Use Tests Results, having at least a first and a second member, such that the first member of said Elemental Set of End-Use Test Results corresponds to said first member of said Elemental Set of Samples and said second member of said Elemental Set of End-Use Tests Results corresponds to said second member of said Elemental Set of Samples, wherein said first member of each set is not the same as the second member of each set;

selecting an Elemental Set of Intermediate Tests having a plurality of members;

obtaining from said selected Elemental Set of Intermediate Tests, a set of Intermediate Test Results;

subjecting the Intermediate Test Results, individually or in combination, to regression analysis to determine which of the members of the Elemental Set of Intermediate Tests is predictive of the Elemental Set of End-Use Test Results for the Elemental Set of Samples; and outputting the members of the Elemental Set of Intermediate Tests from the regression analysis that are predictive of the Elemental Set of End-Use Test Results for the Elemental Set of Samples.

2. The method of claim 1 wherein the Elemental Set of Intermediate Tests is selected from tests capable of producing substantial quantities of data over a broad range.

3. The method of claim 2 wherein the regression analysis is selected from generalized linear regression analysis and non-liner regression analysis.

4. The method of claim 2 wherein the regression analysis is a neural net regression analysis.

5. The method of claim 2 wherein the Intermediate Test Results are obtained by high throughput experimentation.

6. A method for predicting whether a candidate sample will meet an Elemental Set of End-Use Test Results comprising:

(a) using the method in any one of claims 1 to 5 to determine which members, individually or in combination, of an Elemental Set of Intermediate Tests are predictive of an Elemental Set of End-Use Test Results;

(b) performing each of said tests determined in step (a) on each of the members of said Elemental Set of Samples to obtain Intermediate Test Results; and (c) comparing the Intermediate Test Results of step (b) to the Elemental Set of End-Use Test Results whereby conformance is predictive of the candidate sample meeting the Elemental Set of End-Use Test results.

7. A method for predicting whether candidate lubricant samples will pass a selected end use test for lubricants comprising:

(a) determining which individual or combination of a plurality of intermediate tests provides a test result that correlates with a pass/fail criteria for the selected end-use test for lubricants;

(b) subjecting the candidate lubricant samples to the individual or combination of a plurality of intermediate tests determined in step (a);

(c) comparing the test result of the candidate lubricant samples with the pass/fail criteria thereby determining whether the candidate lubricant samples will pass the selected end-use test; and (d) outputting the candidate lubricant samples which pass and fail the pass/fail criteria of the selected end-use test determined in step (c).

8. The method of claim 7 wherein the intermediate tests are selected from the group consisting of tests designed to provide, in a laboratory environment, a measure of a property or performance feature of the lubricant sample.

9. The method of claim 8 wherein the property or performance feature is at least one of wear, friction, viscosity, oxidation stability, thermal stability, sludge, varnish formation, deposit formation, elastomer compatibility, volatility, corrosion, rust, miscibility or solubility, visual appearance, chemical composition, scuffing, acidity increase, soot formation, storage stability, hydrolytic stability, color-light stability, low temperature fluidity, demulsibility, emulsibility, foam formation, air entrainment and acute toxicity.

10. The method of claim 8 wherein the intermediate tests are selected from the group consisting of ASTM tests, SAE (Society of Automotive Engineers) tests, and combinations thereof, wherein the SAE tests are defined in SAE Technical Paper 851797 entitled "Development of a High Temperature Jet Engine Oil—Laboratory and Field Evaluation".

11. A method to determine which combination of members of an Elemental Set of Intermediate Tests have a high correlation with an Elemental Set of End-Use Test Results, the method comprising:
    obtaining for each of a plurality of Samples a set of Intermediate Test Results from said Elemental Set of Intermediate Tests;
    obtaining for each of said plurality of Samples an Elemental Set of End-Use Test Results;
    selecting from said Set of Intermediate Tests two or more members which in combination correlate most closely with said Elemental Set of End-Use Test Results for each of said plurality of Samples; and
    outputting the selected two or more members which in combination correlate most closely with said Elemental Set of End-Use Test Results for each of said plurality of Samples.

12. The method of claim 11 wherein said combination of said Set of Intermediate Tests is selected by randomly combining two or more members of said Set of Intermediate Tests and determining how closely the combination correlates with said Elemental Set of End-Use Test Results and repeating the procedure with other random sets to determine which combination corresponds more closely.

13. The method of claim 12 wherein said combination is selected using a variable selection algorithm.

14. The method of claim 13 wherein the algorithm is an all possible combination algorithm.

15. The method of claim 14 wherein the algorithm is a genetic algorithm.

16. The method of claim 15 wherein said Elemental Set of End-Use Test Results is obtained by subjecting said Samples to said Intermediate Tests using high throughput experimentation.

17. The method of claim 15 further comprising formulating the predicted blend and testing the blend using said combination of Intermediate Tests for compliance with a pass result for said End-Use Test.

18. The method of claim 16 further comprising repeating said selecting, formulating and testing steps until a pass result is achieved.

19. A method for selecting components and component amounts in lubricants, functional fluids or greases comprising:
    obtaining for a plurality of blends of lubricants, functional fluids or greases with varying components and component levels a plurality of Intermediate Test Results from a set of Intermediate Tests and at least one End-Use Test Result from an End-Use Test;
    determining which combination of two or more Intermediate Tests for each blend correlates with a pass result for said End-Use Test;
    identifying the component levels for each blend that corresponds to an End-Use Test Result;
    applying a selection algorithm to the components or mixture of components and levels to predict new blends that will pass said End-Use Test; and
    outputting the components or mixture of components and levels of new blends predicted to pass said End-Use Test.

20. The method of claim 19 wherein the intermediate tests are selected from the group consisting of tests designed to provide, in a laboratory environment, a measure of a property or performance feature of the lubricant sample.

21. The method of claim 20 wherein the property or performance feature is at least one of wear, friction, viscosity, oxidation stability, thermal stability, sludge, varnish formation, deposit formation, elastomer compatibility, volatility, corrosion, rust, miscibility or solubility, visual appearance, chemical composition, scuffing, acidity increase, soot formation, storage stability, hydrolytic stability, color-light stability, low temperature fluidity, demulsibility, emulsibility, foam formation, air entrainment and acute toxicity.

22. The method of claim 19 further comprising subjecting the blend to said End-Use Test to determine actual correlation.

* * * * *